US008137270B2

(12) United States Patent
Keenan et al.

(10) Patent No.: US 8,137,270 B2
(45) Date of Patent: Mar. 20, 2012

(54) METHOD AND SYSTEM FOR PROCESSING DATA FROM AMBULATORY PHYSIOLOGICAL MONITORING

(75) Inventors: Desmond B. Keenan, Santa Barbara, CA (US); Michael Coyle, Ventura, CA (US)

(73) Assignee: adidas AG, Herzogenaurach (DE)

( * ) Notice: Subject to any disclaimer, the term of this patent is extended or adjusted under 35 U.S.C. 154(b) by 1914 days.

(21) Appl. No.: 10/991,877

(22) Filed: Nov. 18, 2004

(65) Prior Publication Data
US 2005/0240087 A1 Oct. 27, 2005

Related U.S. Application Data

(60) Provisional application No. 60/523,495, filed on Nov. 18, 2003, provisional application No. 60/586,347, filed on Jul. 8, 2004.

(51) Int. Cl.
*A61B 5/00* (2006.01)
*A61B 5/02* (2006.01)
*A61B 5/08* (2006.01)
*A61B 5/103* (2006.01)

(52) U.S. Cl. ........ 600/301; 600/300; 600/508; 600/529; 600/534; 600/595

(58) Field of Classification Search .......... 600/534, 600/535
See application file for complete search history.

(56) References Cited

U.S. PATENT DOCUMENTS

| 4,016,868 A | 4/1977 | Allison |
| 4,308,872 A | 1/1982 | Watson et al. |
| 4,373,534 A | 2/1983 | Watson |
| 4,433,693 A | 2/1984 | Hochstein |
| 4,452,252 A | 6/1984 | Sackner |
| 4,456,015 A | 6/1984 | Sackner |
| 4,648,407 A | 3/1987 | Sackner |
| 4,753,088 A | 6/1988 | Harrison et al. |
| 4,777,962 A | 10/1988 | Watson et al. |
| 4,800,495 A | 1/1989 | Smith |
| 4,807,640 A | 2/1989 | Watson et al. |
| 4,815,473 A | 3/1989 | Watson et al. |
| 4,817,625 A | 4/1989 | Miles |
| 4,834,109 A | 5/1989 | Watson |
| 4,860,766 A | 8/1989 | Sackner |

(Continued)

FOREIGN PATENT DOCUMENTS

WO WO 97/47236 A1 12/1997

(Continued)

OTHER PUBLICATIONS

P. Anderer et al., "Artifact Processing in Computerized Analysis of Sleep EED—A Review" Neuropsychobiology, vol. 40, pp. 150-157 (1999).

(Continued)

*Primary Examiner* — Patricia Mallari
(74) *Attorney, Agent, or Firm* — Sterne, Kessler, Goldstein & Fox PLLC

(57) ABSTRACT

This invention provides methods and systems for the analysis of data returned from monitoring multiple physiological parameters of a subject, especially from ambulatory multiple parameter monitoring. The methods and systems remove motion artifacts from signals and separate multiple components of single signals due to two or more physiological systems or processes. Each output signal is are preferably free from motion artifacts and reflects primarily functioning of only a single physiological system or process.

10 Claims, 10 Drawing Sheets

U.S. PATENT DOCUMENTS

Figure 1A:
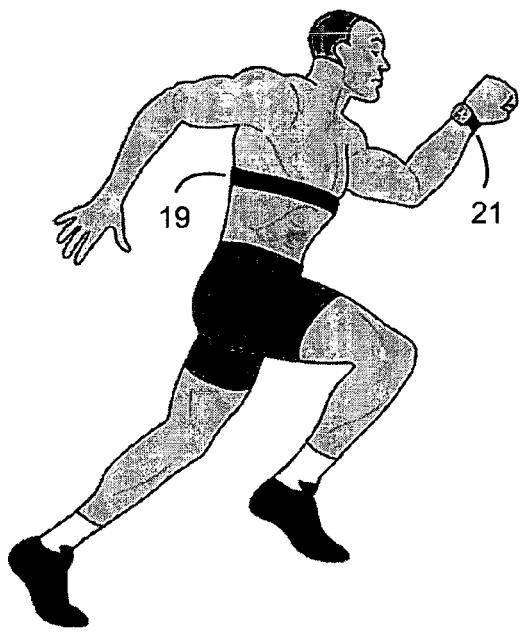

| | | | |
|---|---|---|---|
| 4,911,167 A | 3/1990 | Corenman et al. | |
| 4,934,372 A | 6/1990 | Corenman et al. | |
| 4,960,118 A | 10/1990 | Pennock | |
| 4,966,155 A | 10/1990 | Jackson | |
| 4,986,277 A | 1/1991 | Sackner | |
| 5,007,427 A | 4/1991 | Suzuki et al. | |
| 5,040,540 A | 8/1991 | Sackner | |
| 5,074,129 A | 12/1991 | Matthew | |
| 5,159,935 A | 11/1992 | Sackner et al. | |
| 5,178,151 A * | 1/1993 | Sackner | 600/485 |
| 5,224,479 A | 7/1993 | Sekine | |
| 5,301,678 A | 4/1994 | Watson et al. | |
| 5,331,968 A | 7/1994 | Williams et al. | |
| 5,348,008 A | 9/1994 | Bornn et al. | |
| 5,353,793 A | 10/1994 | Bornn et al. | |
| 5,416,961 A | 5/1995 | Vinay | |
| 5,447,164 A | 9/1995 | Shaya et al. | |
| RE35,122 E | 12/1995 | Corenman et al. | |
| 5,533,511 A | 7/1996 | Kaspari et al. | |
| 5,544,661 A | 8/1996 | Davies et al. | |
| 5,564,429 A | 10/1996 | Bornn et al. | |
| 5,584,295 A | 12/1996 | Muller et al. | |
| 5,588,425 A | 12/1996 | Sackner et al. | |
| 5,820,567 A | 10/1998 | Mackie | |
| 5,913,830 A | 6/1999 | Miles | |
| 5,991,922 A | 11/1999 | Banks | |
| 6,002,952 A | 12/1999 | Diab et al. | |
| 6,015,388 A | 1/2000 | Sackner et al. | |
| 6,018,677 A | 1/2000 | Vidrine et al. | 600/520 |
| 6,047,203 A | 4/2000 | Sackner et al. | |
| 6,066,093 A | 5/2000 | Kelly et al. | |
| 6,067,462 A | 5/2000 | Diab et al. | |
| 6,223,072 B1 | 4/2001 | Mika et al. | |
| 6,254,551 B1 | 7/2001 | Varis | |
| 6,261,238 B1 | 7/2001 | Gavriely | |
| 6,341,504 B1 | 1/2002 | Istook | |
| 6,361,501 B1 | 3/2002 | Amano et al. | |
| 6,413,225 B1 | 7/2002 | Sackner et al. | |
| 6,436,057 B1 | 8/2002 | Goldsmith | |
| 6,449,504 B1 | 9/2002 | Conley et al. | |
| 6,506,153 B1 * | 1/2003 | Littek et al. | 600/301 |
| 6,551,252 B2 | 4/2003 | Sackner et al. | |
| 6,604,115 B1 | 8/2003 | Gary et al. | |
| 6,633,772 B2 | 10/2003 | Ford et al. | |
| 6,699,194 B1 | 3/2004 | Diab et al. | |
| 6,702,752 B2 | 3/2004 | Dekker | |
| 6,709,402 B2 | 3/2004 | Dekker | |
| 6,721,594 B2 | 4/2004 | Conley et al. | |
| 6,783,498 B2 | 8/2004 | Sackner et al. | |
| 6,801,916 B2 | 10/2004 | Roberge et al. | |
| 6,881,192 B1 | 4/2005 | Park | |
| 7,001,337 B2 | 2/2006 | Dekker | |
| 7,104,962 B2 | 9/2006 | Lomask et al. | |
| 7,604,603 B2 | 10/2009 | Sackner et al. | |
| 2003/0187341 A1* | 10/2003 | Sackner et al. | 600/388 |
| 2004/0019289 A1 | 1/2004 | Ross | |
| 2004/0249299 A1 | 12/2004 | Cobb | |
| 2005/0054941 A1 | 3/2005 | Ting et al. | |
| 2005/0119586 A1 | 6/2005 | Coyle et al. | 600/538 |
| 2005/0228234 A1 | 10/2005 | Yang | |
| 2008/0027341 A1 | 1/2008 | Sackner et al. | |

FOREIGN PATENT DOCUMENTS

| | | |
|---|---|---|
| WO | WO 00/71027 A1 | 11/2000 |
| WO | WO 01/25802 A2 | 4/2001 |
| WO | WO 01/78577 A2 | 10/2001 |
| WO | WO 2004/091503 A2 | 10/2004 |
| WO | WO2005115242 | 12/2005 |

OTHER PUBLICATIONS

H.J. Park et al., "Automated Detection and Elimination of Periodic ECG Artifacts in EEG Using The Energy Interval Histogram Method", IEEE Transactions on Biomedical Engineering, vol. 49, No. 12 pp. 1526-1533 (2002).

Micro-Coax, "About Micro-Coax", www.microcoax.com (visited Aug. 2004).

T.G. McNaughton et al., "Metallized Polymer Fibers As Leadwires and Intrafascicular Microelectrodes", J. Neurosci. Methods, 70(1):103-10 (1996), Abstract only.

Signal Consulting Inc., "Inductance of Circular Loop", www.sigcon.com (visited Aug. 2005).

Gore Electronic Expanded, "PTFE Insulation Material", www.goreelectronics.com (visisted Aug. 2004).

R.E. Klabunde, "Electrocardiogram (EKG, ECG)", Cardiovascular Physiology Concepts, www.cvphysiology.com (visited Mar. 2005).

M. Bonnet et al., "EEG Arousals: Scoring Rules and Examples", American Sleep Disorders Association and Sleep Research Society, vol. 15, No. 2 pp. 173184 (1992).

R.A.J.M. Van Dijk et al., "Determinants of Brachial Artery Mean 24 h Pulse Pressure in Individuals With Type II Diabetes Mellitus and Untreated Mild Hypertension," Clinical Science vol. 102, pp. 177-186 (2002).

S. Pietraszek et al., "Simple Telemetry System for ECG Recording", Polish J Med Phys & Eng, vol. 8(3): pp. 193-198 (2002).

R. Almeida et al., "Wavelet Transform Based Matlab System for the Detection and Delineation of QRS Complexes in Ambulatory ECG Recordings", Sixth Portuguese Conference on Biomedical Engineering (2001).

R. S. H. Istepanian et al., "Microcontroller-Based Underwater Acoustic ECG Telemetry System", IEEE Transactions on Information Technology in Biomedicine, vol. 1, No. 2, Jun. 1997, pp. 150154.

J.P. Niskanen et al., "Software for Advanced HRV Analysis", University of Kuopio; Department of Applied Physics Report Series, Report No. Feb. 2002, pp. 1-11.

D. E. O'Donnell, "Ventilatory Limitations in Chronic Obstructive Pulmonary Disease", Medicine & Science in Sports & Exercise, pp. S647-S655, (2001).

D. E. O'Donnell et al., "Dynamic Hyperinflation and Exercise Intolerance in Chronic Obstructive Pulmonary Disease", Am. J. Respir. Crit. Care Med., vol. 164, pp. 770-777, (2001).

J.M. Marin et al., "Inspiratory Capacity, Dynamic Hyperinflation, Breathlessness, and Exercise Performance During the 6-Minute-Walk Test in Chronic Obstructive Pulmonary Disease", Am. J. Respir. Crit. Care Med., vol. 163., pp. 1395-1399, (2001).

M.A. Coyle et al., "Home Measurement of Cough Indicates Circadian Frequency Pattern and Abnormal Distribution During Sleep", LifeShirt System, study sponsored by Pfizer, Inc., Jun. 2004.

Grossman et al., A Comparison of Three Quantification Methods for Estimation of Respiratory sinus Arrhythmia:, Methodology, vol. 27, No. 6, pp. 702-714.

Bianchi et al., "Extraction of the Respiration Influence from the Heart Rate Variability Signal by Means of Lattice Adaptive Filter", IEEE, pp. 121-122.

Fahrenberg et al., "Origins and Developments of Ambulatory Monitoring and Assessment," 2001, Chapter 35, pp. 587-616.

Sagie et al., "An Improved Method for Adjusting the QT Interval for Heart Rate," (the Framingham Heart Study), The American Journal of Cardiology, vol. 70, Sep. 15, 1992, pp. 797-801.

6th Portuguese Conference on Biomedical Engineering, "BioEng' 2001 Conference Papers", (Jun. 2001) 6 pages.

Keenan et al., "Adaptive Filtering of Heart Rate Signals for an Improved Measure of Sympathovagal Balance," Jan. 1, 2005, 8 pages.

Grossman et al., A Comparison of Three Quantification Methods for Estimation of Respiratory sinus Arrhythmia:, Methodology, vol. 27, No. 6, pp. 702-714, Nov. 1990.

Bianchi et al., "Extraction of the Respiration Influence from the Heart Rate Variability Signal by Means of Lattice Adaptive Filter", IEEE, pp. 121-122, (c) 1994.

* cited by examiner

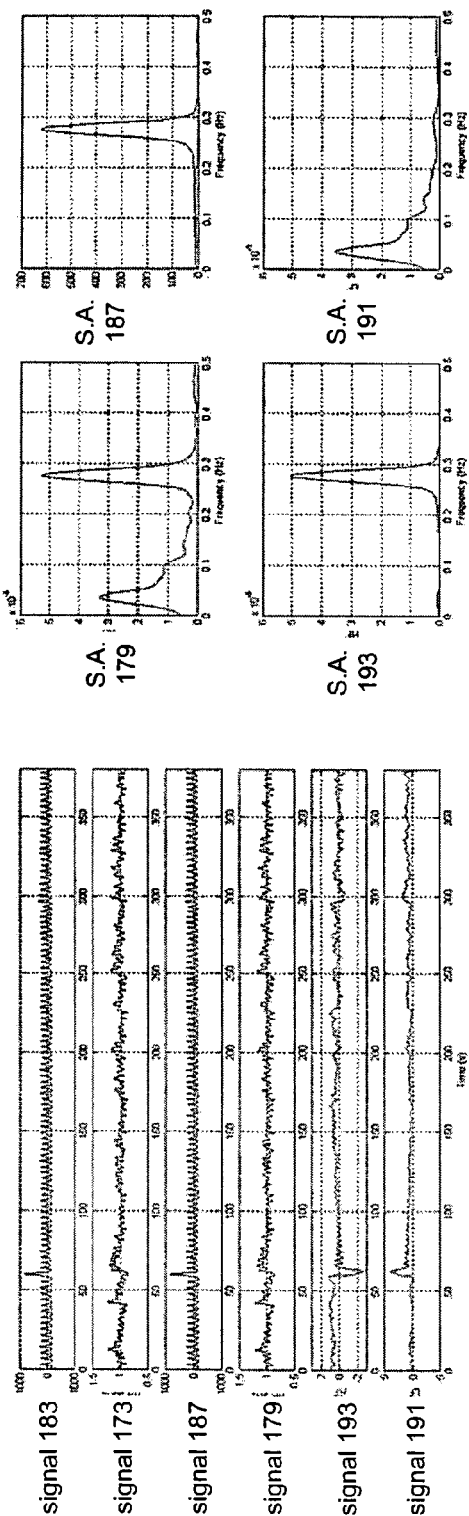
FIG. 10A
FIG. 10B
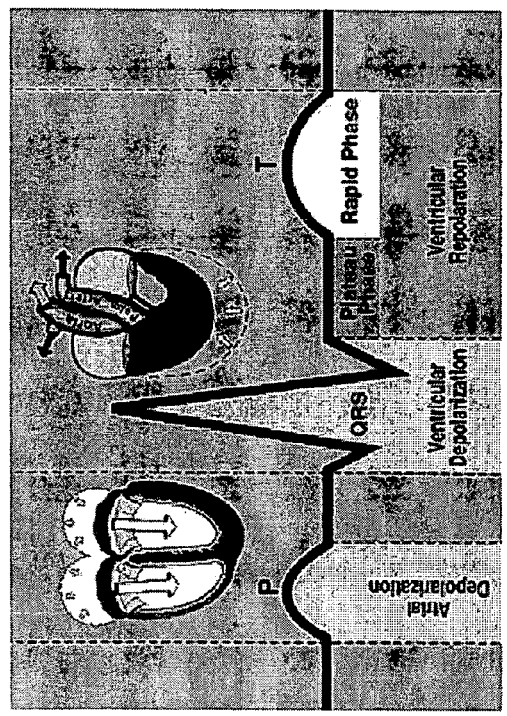
FIG. 11

METHOD AND SYSTEM FOR PROCESSING DATA FROM AMBULATORY PHYSIOLOGICAL MONITORING

This application claims the benefit of U.S. Provisional Application No. 60/523,495, filed Nov. 18, 2003 (titled: Systems and Methods for Improved Determination of Cardiac Rate Parameters), and U.S. Provisional Application 60/586,347, filed Jul. 8, 2004 (titled: Method and System for Extracting Cardiac Parameters From Plethysmographic Signals Using Adaptive Signal Processing). Both of these provisional applications are included by reference herein in the entireties for all purposes.

1. FIELD OF THE INVENTION

The present invention relates to the field of processing signals obtained from non-invasive physiological monitoring, and especially from non-invasive monitoring which gathers multiple physiological parameters while permitting relatively free subject motion. The present invention provides improved, robust systems and methods for processing such signals.

2. BACKGROUND OF THE INVENTION

Monitoring a subject's physiological parameters is routine in the clinic and in the hospital. Because of the interdependence of physiological and other bodily processes, monitoring of multiple related physiological parameters (referred to herein as "multiple parameter monitoring" or "MPM") is advantageous is known in these environments.

Recent developments in sensors and sensor systems now increasingly allow single and multiple parameter physiological monitoring to move out of the controlled environments of the clinic or hospital and into less constrained environments where the subject may engage in normal activities. MPM is now possible in the subject's normal environments where the subject is carrying out normal activities with little or no constraint. "Ambulatory monitoring", as such monitoring is known in the art, thereby encompasses the monitoring of physiological parameters during normal daily activities, including work activities, and also encompasses monitoring during unconstrained sleep. For example, during "ambulatory monitoring", a subject may be walking, running, generally exercising, engaging in athletics, and the like; a subject may also be working at either sedentary or active tasks; a subject may also be resting, sitting, reclining, sleeping, and the like. In this application, the term "ambulatory monitoring" is used and understood to refer to monitoring physiological parameters during the broad range of subject activities, and the term "ambulatory multiple parameter monitoring" (or "ambulatory MPM") is used to refer monitoring multiple physiological parameters during such activities.

A recent example of an ambulatory monitoring system is described in U.S. Pat. No. 6,551,252 B1, issued Apr. 23, 2003. This patent describes monitoring systems and methods comprising comfortable garments that serve as platforms for sensors of multiple physiological parameters. Ambulatory monitoring then merely requires a subject to wear such a comfortable garment.

However, processing signals recorded during ambulatory MPM signals to extract useful physiological information during is considerably often more difficult than similar processing of signals obtained during in-clinic or in-hospital monitoring. For example, characteristics such as frequency spectrum and amplitude of the signals recorded during ambulatory monitoring can vary unpredictably as the monitored subject's activity varies unpredictably. Processing must be capable of handling such unpredictable signal characteristics. In addition, unconstrained subject activities can introduce considerable artifact and noise in ambulatory monitoring signals which is also of variable characteristics. Further, non-invasive sensors usually used for ambulatory monitoring often output signals sensitive to multiple physiological systems or processes. In contrast, few is any of these problems arise during controlled in-clinic or in-hospital monitoring. Signal recording during the latter monitoring usually have only limited variability with limited artifact and noise, and sensors used can be designed for sensitivity to single physiological systems or processes.

A recent example of the complexities of ambulatory signal processing is U.S. Pat. No. 6,783,498 B2. This patent describes systems and methods for determining cardiac function from signals obtained using non-invasive sensors during ambulatory monitoring. Because the cardiac signals of interest are usually have small amplitude and are usually obscured by considerably larger amplitude respiratory and other undesired signals, careful processing is required to extract useful cardiac information.

Accordingly, the art is in need of improved processing techniques broadly applicable to signals from ambulatory MPM monitoring that provide robust and reliable extraction of useful physiological information from such signals.

A number of references are cited herein, the entire disclosures of which are incorporated herein, in their entirety, by reference for all purposes. Further, none of these references, regardless of how characterized above, is admitted as prior to the invention of the subject matter claimed herein.

3. SUMMARY OF THE INVENTION

Objects of this invention include systems and methods for improved robust and reliable extraction of physiological information from signals gathered during concurrent monitoring of multiple physiological (MPM) parameters of a subject, especially MPM monitoring when the subject is carrying out normal waking and sleeping activities.

Concurrent monitoring of multiple physiological parameters is advantageous (even if only one physiological system is of interest) because of the known interdependence of the body's physiological systems. And if two or more physiological systems or their interactions are of interest, monitoring multiple parameters is necessary. Ambulatory monitoring is also advantageous. For patients with disease, ambulatory monitoring can aid a physician in their tracking and treatment. Ambulatory monitoring is also useful in diagnosis of, for example, sleep disorders. Also, even for subjects without disease, minute-by-minute physiological monitoring can be useful. For example, monitoring of individuals or workers exposed to physiological stress or danger, such as rescue personnel, emergency response personnel, military personnel, and the like, can help prevent their injury. For athletes and for those seeking general fitness, ambulatory monitoring can track the progress of training programs and guide future effort. Additional applications are known in the art and are likely to be developed in the future.

However, processing ambulatory signals presents novel problems arising in part because these signals can be far from the ideal that normally expected in controlled and sedentary in-clinic or in-hospital monitoring. For example, monitoring during normal subject activities without the attention of specialized personnel requires that sensors and monitoring systems generally be chosen or designed to meet subject concerns, such as subject acceptability, unobtrusiveness (to the extent that a subject can become unaware of their presence), ease of use (so that the subject can use them without trained assistance), and the like. Meeting these subject concerns may preclude the use of technically optimal but often invasive sensors.

Therefore ambulatory MPM signals often include significant artifact and/or noise, such as motion artifacts generated during subject activity. Further, a single ambulatory MPM sensor signal often includes mixed contributions from several physiological systems or processes. Extracting useful physiological information then requires separation of such mixed components, which is often difficult because the contributing components may have differing amplitudes and/or overlapping frequency spectrums. Moreover, MPM signal characteristics, such as frequency spectra are usually not stationary, but vary with subject activity level. Signal processing techniques with fixed parameters selected for signals with expected characteristics, for example a bank of fixed frequency filters, may work only at a few activity levels but not at most other activity levels.

This invention solves these problems by jointly processing signals from multiple (two or more) sensors using signal processing techniques that adapt to unpredictable and changing signal characteristics. Multiple input signals each with mixed physiological components are jointly processed into output signals each with a single physiological component. Motion and other artifacts are minimized by jointly processing sensor signals and "artifact" signals correlated with the artifact sources. Adaptive techniques also avoid the need to know signal characteristics in advance, as these characteristics may instead be learned during a brief initialization period. It has been found important for improved adaptive processing performance that the signals being jointly processed by periodically sampled and the same frequency, and even coincidentally sampled if possible. Further, the adaptive techniques used in this invention are preferably configured with response times to varying signal characteristics adequate to physiological systems being monitored. Signals arising from normal ambulatory activities generally vary over periods from several seconds (15 secs or 30 secs) to minutes (1 min or 2 min) or more. Since adaptation rates depend on sampling frequency, filter memory times, rates of convergence, and the like, the signal and filter characteristics are selected in individual cases for adequate physiological response.

The present invention may be applied to monitoring in sedentary, or controlled, environments, as well as to monitoring which does not constrain subject activities. Such non-constraining monitoring systems allow substantially free subject motion during waking and sleeping. The present invention may be applied to signals generated by a variety of sensors, preferably non-invasive sensors suitable for ambulatory, unassisted monitoring in a variety of environments. Sensors are preferably sufficiently accurate and precise so that contributions of the multiple physiological systems and/or processes each have useful signal to noise ratios. For example, if one input signal includes a first system's signals with only 5% of the amplitude of a second system, then a useful sensor will have a relative accuracy and/or precision of 1%, and preferably 0.5%, and more preferably 0.1% or 0.05% or lower. For input to the present invention, sensor signals are digitized at periodic, preferably fixed. Sample rates, amplitude quantization, and the like are chosen as is known in the arts so that the digitized signal represents measured signal in a predictable and fixed manner, preferably without aliasing spectra or amplitudes.

In one embodiment the invention includes a method for processing sensor signals arising from a plurality of sensors sensitive to a plurality of physiological systems or processes of a monitored subject, the method comprising adaptively enhancing desired physiological components relative to undesired artifact components in one or more sensor signals monitored from said subject during periods comprising unconstrained activity; and adaptively enhancing components sensitive to desired physiological systems or processes relative to components sensitive to other undesired physiological systems or processes in one or more of the sensor signals that have adaptively enhanced physiological components.

Further aspects of this embodiment include: retrieving one or more sensor signals from a wearable construction comprising one or more sensors; that the physiological systems or processes include one or more of respiratory activity, or cardiac mechanical activity, or cardiac electrical activity, or electroencephalographic activity, or motion activity; that the physiological systems or processes include one or more of temperature activity, or blood saturation activity, or vocal activity, or electro-oculogram activity, or electro-myogram activity; that enhancing components in sensor signals further includes processing said sensor signals jointly with one or more reference sensor signals, wherein said sensor signals and said reference sensor signals are sampled and/or re-sampled at the same sampling rate; and that the one or more reference signals include signals sensitive to subject motion activity.

Further aspects of this embodiment include: that the one or more reference signals sensitive to said undesired physiological systems or processes; that the reference sensor signals include components correlating with said undesired components in said sensor signals, and said sensor signals and said reference signals being sampled and/or re-sampled at the same sampling rate; further including re-sampling one or more sensor signals at the same sampling rate; that enhancing components sensitive to said desired physiological systems or processes includes joint processing with one or more reference signals sensitive to said undesired other physiological systems or processes; and that enhancing components sensitive to desired physiological components or processes in one or more sensor signals further includes generating additional signals in which are enhanced components sensitive to said other undesired physiological systems or processes, whereby said desired and said undesired physiological components are enhanced in separate output signals.

In one embodiment the invention includes a system for processing physiological sensor signal data comprising: a wearable construction comprising one or more sensors sensitive to one or more physiological systems or processes including motion activity; and computer memory comprising computer instructions to retrieve a plurality of physiological sensor signals from said wearable construction when worn by a monitored subject during periods comprising unconstrained activities, said retrieved sensor signals comprising reference signals sensitive to subject motion activity; and to enhance desired physiological components relative to undesired motion artifact components in one or more retrieved sensor signals, said enhancing comprising adaptively processing said sensor signals jointly with one or more of said reference signals in order to reduce an error signal.

Further aspects of this embodiment include: that the reference sensors include one or more accelerometers; further including de-trending one or more of said sensor signals and/or said reference signals; and that the error signal is a difference between processed retrieved sensor signals and processed reference sensor signals.

In one embodiment the invention includes a system for processing physiological sensor signal data comprising a wearable construction comprising one or more sensors sensitive to physiological systems or processes comprising cardiac pulsation activity and respiratory activity; and computer memory comprising computer instructions to retrieve sensor signals from said wearable construction when worn by a monitored subject during periods comprising unconstrained activities, said retrieved sensor signals comprising cardiac signals with cardiac pulsation components and respiratory signals with respiratory activity components; and to enhance desired cardiac components relative to undesired respiratory components in said cardiac signals, said enhancing comprising adaptively processing said cardiac signals jointly with said respiratory signals in order to reduce an error signal.

Further aspects of this embodiment include: that the said cardiac signals include cardiac pulsation components and respiratory activity components with relative amplitudes larger than relative amplitudes of cardiac pulsation components and respiratory activity components in said respiratory signals; that the error signal is a difference between processed cardiac signals and processed respiratory signals; that the instructions further time domain filter said cardiac enhanced cardiac signals; that the time domain filtering includes ensemble averaging timed by electrocardiographic R waves; that a value of said ensemble averaged signal at a current time sample includes an average of a current value of said cardiac signal and of values of said cardiac signal at one or more prior time samples, all averaged samples having the same relative position in the cardiac cycle; that the relative position in the cardiac cycle is determined from R-R intervals; that the sensors include at least one size sensor for monitoring respiratory signals and at least one size sensor at a pre-cordial mid-thorax level for monitoring cardiac pulsation signals; that the instructions further extract one or more indicia of cardiac functioning from said enhanced cardiac signal; and that the indicia of cardiac functioning include stroke volume, or cardiac output, or pre-ejection period, or peak ejection rate, or time to peak ejection rate.

In one embodiment the invention includes a system for processing physiological sensor signal data comprising a wearable construction comprising one or more sensors sensitive to physiological systems or processes comprising electroencephalographic (EEG) activity and respiratory activity; and computer memory comprising computer instructions to retrieve sensor signals from said wearable construction when worn by a monitored subject during periods comprising unconstrained activities, said retrieved sensor signals comprising EEG signals and respiratory signals; to estimate respiratory components in said EEG signal by adaptively processing said EEG signals jointly with said respiratory signals in order to reduce an error signal; and to enhance desired EEG components relative to undesired respiratory components in said EEG signals in dependence on said estimated respiratory components.

Further aspects of this embodiment include: low pass filtering said EEG signals using a low pass filter that passes at least those frequencies in the range of frequencies present in respiratory signals; and include removing said estimated respiratory components from said retrieved and unprocessed EEG signal; that removing includes subtraction.

In one embodiment the invention includes a system for processing physiological sensor signal data comprising: a wearable construction comprising one or more sensors sensitive to physiological systems or processes comprising electrocardiographic (ECG) activity and respiratory activity; and computer memory comprising computer instructions to retrieve sensor signals from said wearable construction when worn by a monitored subject during periods comprising unconstrained activities, said retrieved sensor signals comprising ECG signals and respiratory signals; to generate an RR interval signal from said ECG signal comprising data describing successive intervals between successive R-waves; and to estimate respiratory components in said ECG signal by adaptively processing said ECG signals jointly with said respiratory signals in order to reduce an error signal, wherein a high frequency heart rate variability (HF HRV) signal includes said estimated respiratory components, a low frequency heart rate variability (LF HRV) signal includes said error signal.

Further aspects of this embodiment include: that the instructions further de-trend said HF HRV signal and de-trend said LF HRV signal or further de-trend said HF HRV and de-trend said RR interval signal prior to said estimating; that the instructions further spectrally analyze said LF HRV signal and/or said HF HRV signal; that the respiratory signal includes a tidal volume (Vt) signal; that the retrieved respiratory signals include at least one signal from a size sensor at a rib cage (RC) level and at least one signal from a size sensor at an abdominal (AB) level, and wherein the instructions further determine said Vt signal by combining said RC signal and said AB signal; that the instructions further low pass filter said respiratory signal using a low pass filter that passes at least those frequencies in the range of frequencies normally present in respiratory signals, for example, passing signals less than approximately 1.5 Hz; that the error signal is a difference between said processed ECG signals and said processed respiratory signals.

In one embodiment the invention includes a system for processing physiological sensor signal data comprising: a wearable construction comprising one or more sensors sensitive to physiological systems or processes comprising electrocardiographic (ECG) activity and respiratory activity; and computer memory comprising computer instructions to retrieve sensor signals from said wearable construction when worn by a monitored subject during periods comprising unconstrained activities, said retrieved sensor signals comprising ECG signals and respiratory signals; to generate an RR interval signal from said ECG signal comprising data describing intervals between successive R-waves; to estimate respiratory components in said ECG signal by adaptively processing said ECG signals jointly with said respiratory signals in order to reduce an error signal, wherein a low frequency heart rate variability (LF HRV) signal includes said error signal; and to estimate one or more corrected QT intervals independence on QT intervals measured in said ECG signal and on said LF HRV signal.

Further aspects of this embodiment include: that the respiratory signal includes a tidal volume (Vt) signal; that the error signal is a difference between said processed ECG signals and said processed respiratory signals; and that the corrected QT intervals are estimated using a formula substantially similar to:

$$QT_c = \frac{QT}{\sqrt{RR}}$$

or substantially similar to:

$$QT_{LC} = Qt + 0.154(1-RR);$$

In one embodiment the invention includes a computer memory comprising computer instructions for processing sensor signals arising from a plurality of sensors sensitive to a plurality of physiological systems or processes of a monitored subject, by performing: adaptively enhancing desired physiological components relative to undesired artifact components in one or more sensor signals monitored from said subject during periods comprising unconstrained activity; and adaptively enhancing components sensitive to desired physiological systems or processes relative to components sensitive to other undesired physiological systems or processes in one or more of the sensor signals that have adaptively enhanced physiological components. In further aspects the computer memory further includes one or more CD-ROMS or memories accessible to one or more processors.

Further aspects of most embodiments includes one of more of: that the wearable construction includes a band for encircling a body part, or a garment for all or part of the trunk, or a garment for all or part of the trunk and all or part of one or more extremities, or two or more of said bands or said garments, and/or includes one or more inductive plethysmographic sensors; that said activities include one or more of standing, or walking, or running, or climbing, or sitting, or lying, or sleeping, normal daily activities of said subject, or unconstrained by said monitoring; that the functioning of one or more physiological systems or processes varies during subject activity, and wherein sensor signals sensitive to said varying physiological systems or processes have varying signal characteristics; that the sensor signals include size sensor signals sensitive to a rib cage size, or to a mid-thorax size, or to an abdominal size, or to an extremity size; that artifact components include motion artifacts arising from subject activity or electromagnetic interference artifacts;

Further aspects of adaptively enhancing includes one of more of: joint processing of two or more sensor signals sampled and/or re-sampled at the same sampling rate; re-sampling one or more sensor signals at the same sampling rate; reducing an error signal that is a difference between said processed sensor signals and said processed reference sensor signals; adjusting weights of a finite impulse response filter by a least means squares technique; joint processing with one or more reference signals sensitive to subject motion activity.

Further aspects of most embodiments includes one of more of: that the functioning of one or more physiological systems or processes varies during subject activity, and wherein sensor signals sensitive to said varying physiological systems or processes have varying signal characteristics; that the retrieved sensor signals are adaptively processed to enhance desired components relative to artifact components; that the instructions further determine an R-R interval signal by detecting R waves in an electrocardiogram signal sensitive to cardiac electrical activity; discarding detected R waves that occur in an ectopic temporal location; determining said R-R interval signal, and/or interpolating a constructed R wave at the expected temporal position of a discarded ectopic R wave.

Specific embodiments of this invention will be appreciated from the following detailed descriptions and attached figures, and various of the described embodiments are recited in appended claims. In the following, and in the application as a whole, headings are used for clarity and convenience only.

4. BRIEF DESCRIPTION OF THE DRAWINGS

Figure 2:
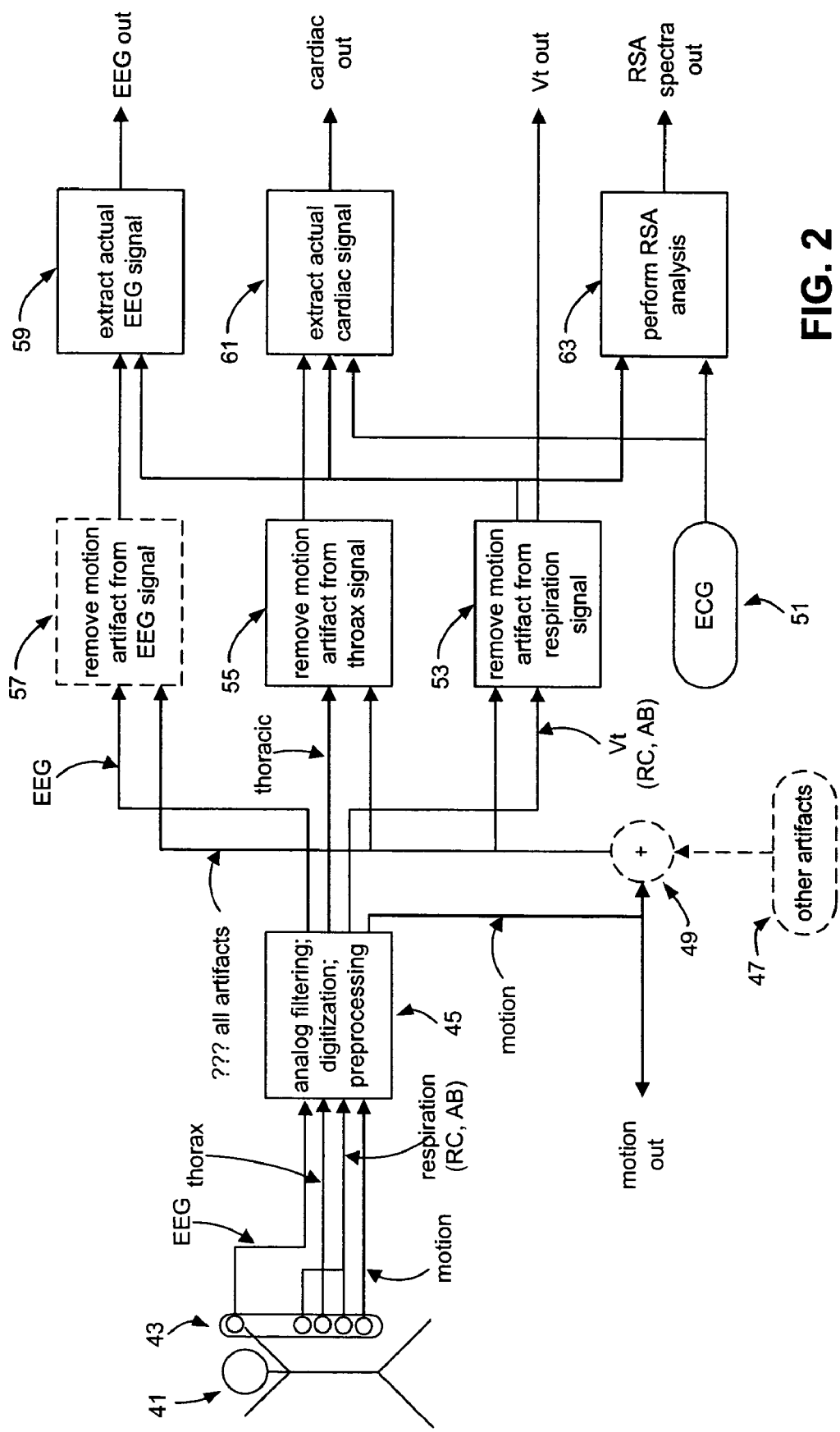
Figure 3A:
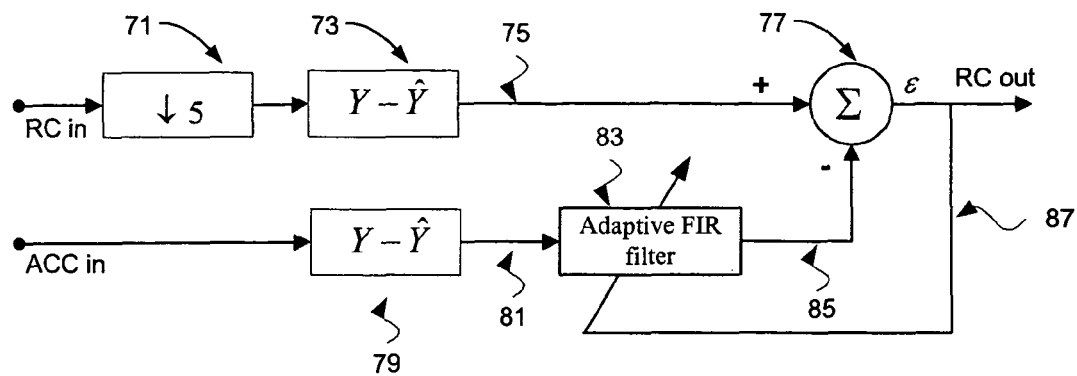
Figure 3B:
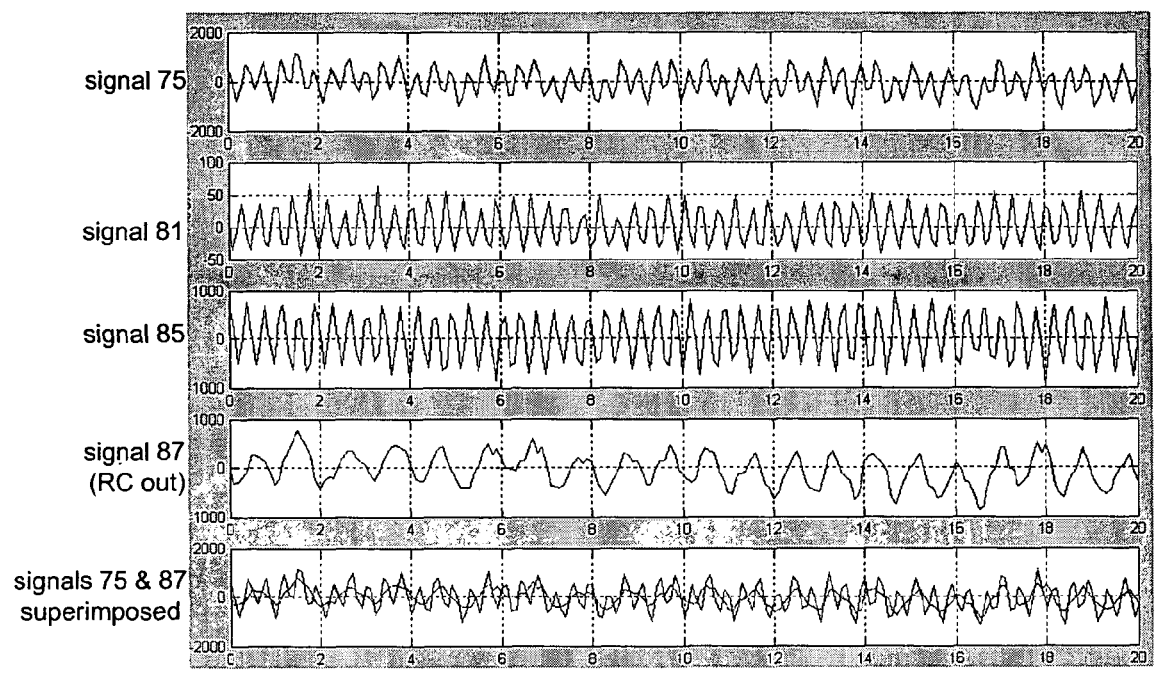
Figure 4:
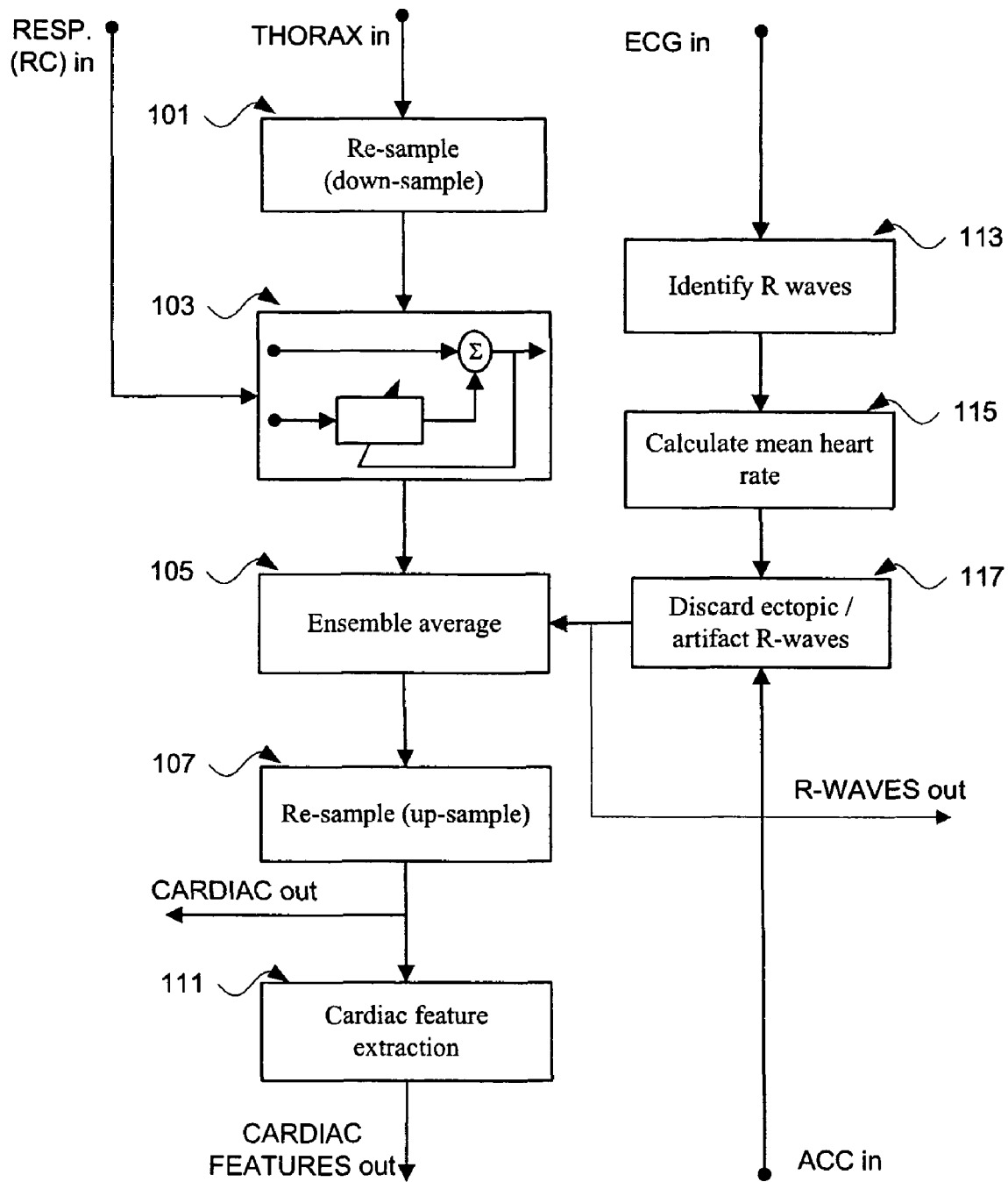
Figure 6A:
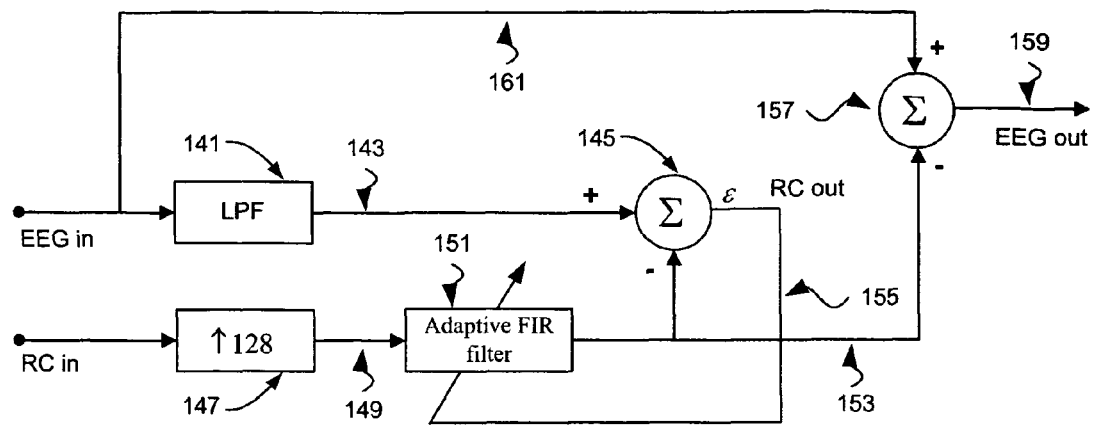
Figure 6B:
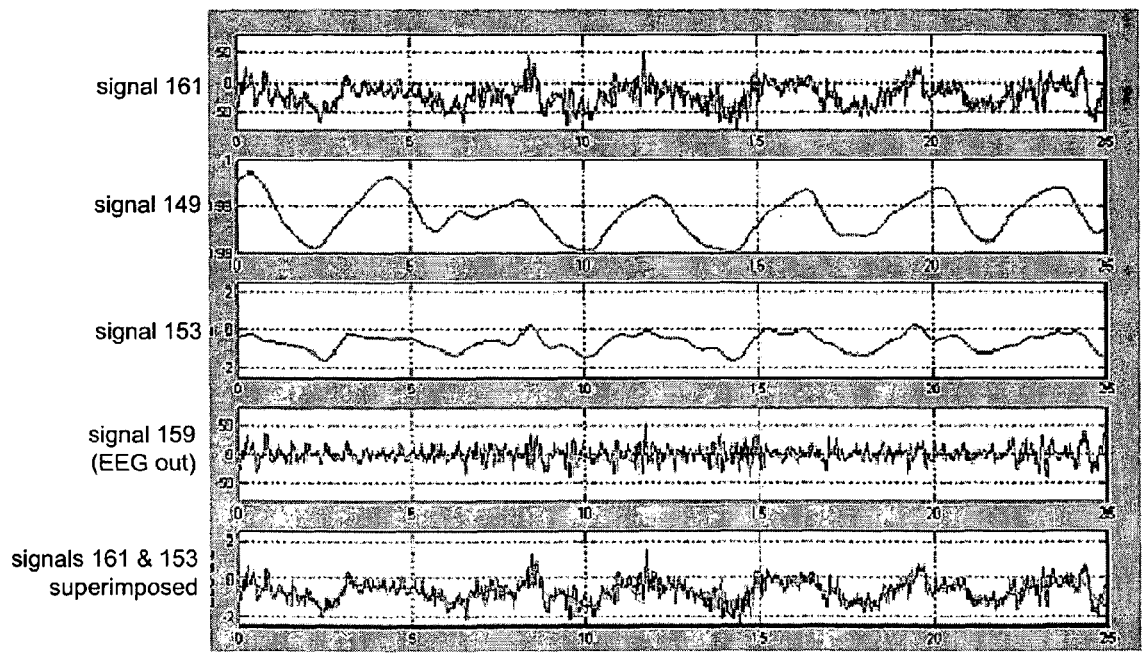
Figure 7:
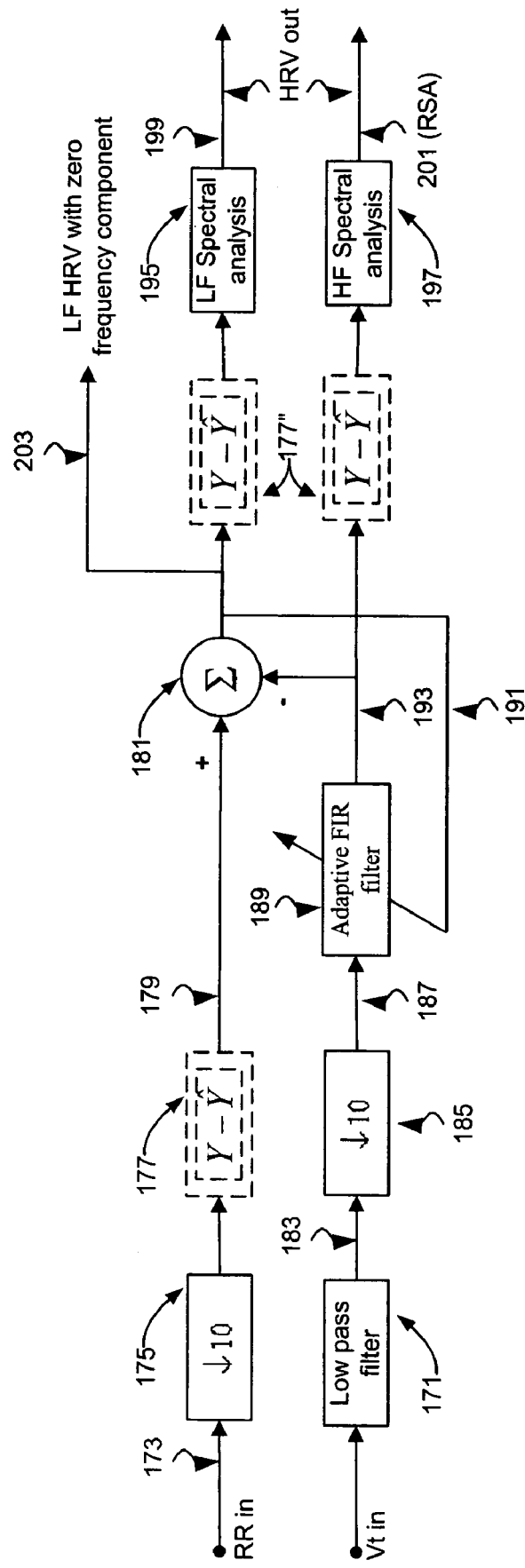
Figure 8B:
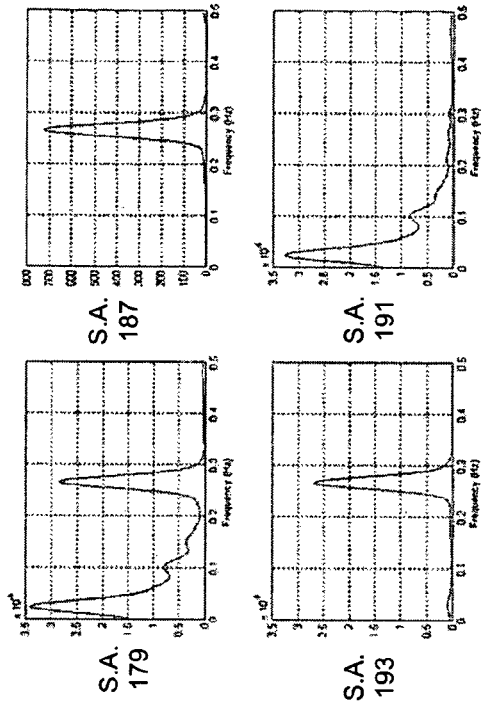
Figure 9B:
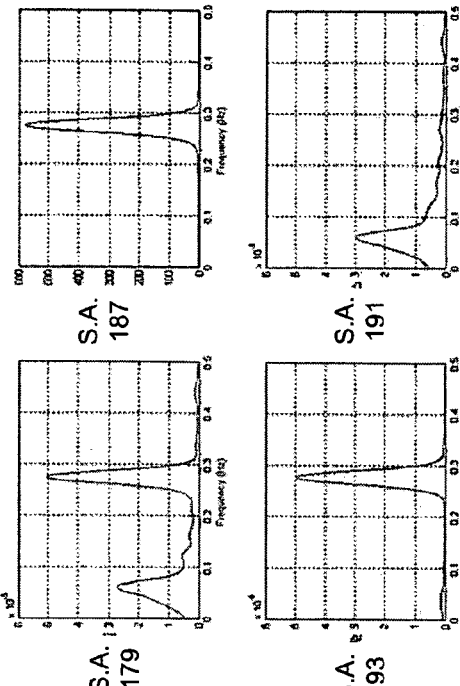
Figure 8A:
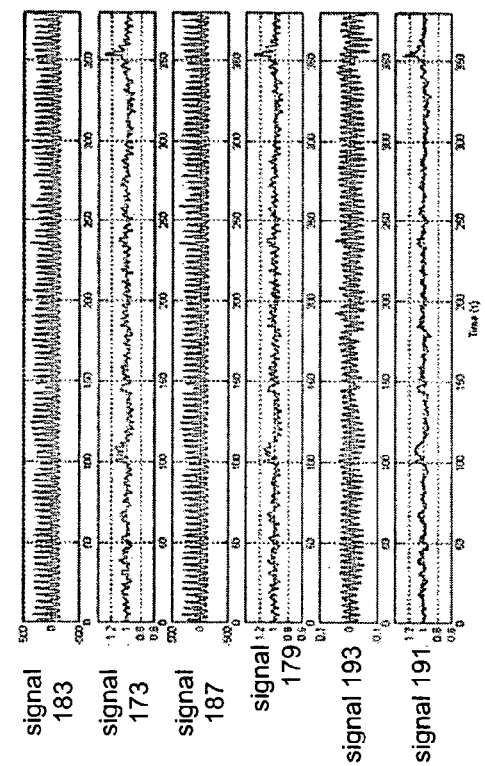
Figure 9A:
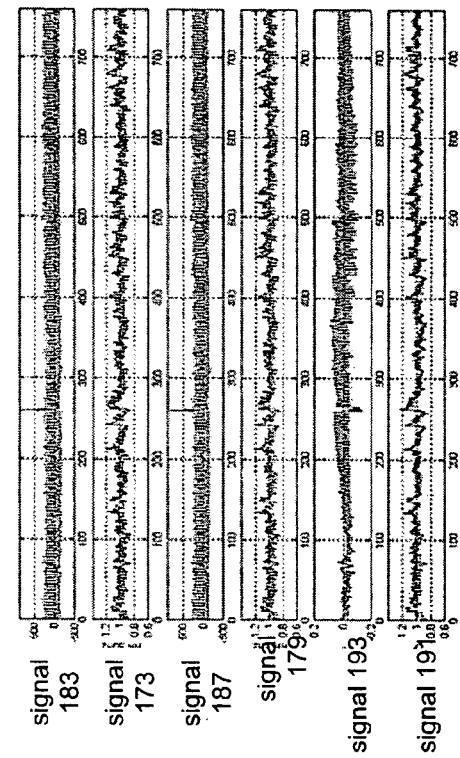

The present invention may be understood more fully by reference to the following detailed description of preferred embodiments of the present invention, illustrative examples of specific embodiments of the invention, and the appended figures in which:

FIGS. 1A-D illustrate exemplary ambulatory multiple parameter monitoring systems of this invention;
FIG. 2 illustrates methods of this invention;
FIGS. 3A-B illustrate methods of motion artifact removal and an example of motion artifact removal;
FIG. 4 illustrates methods of separating respiratory and cardiac signals;
FIGS. 5A-F illustrate an example separating respiratory and cardiac signals;
FIGS. 6A-B illustrate methods of separating respiratory and EEG signals and an example of separating respiratory and EEG signals;
FIG. 7 illustrates methods of analysis of heart rate variability (HRV);
FIGS. 8A-B illustrate an example of HRV analysis;
FIGS. 9A-B illustrate a further example of HRV analysis;
FIGS. 10A-B illustrate a further example of HRV analysis; and
FIG. 11 illustrates an exemplary ECG.

5. DETAILED DESCRIPTION OF THE PREFERRED EMBODIMENTS

Preferred and/or illustrative embodiments of the present invention are described herein. However, the inventive principles of the present invention are not limited to these preferred and/or illustrative embodiments. These principles can be applied more broadly and/or adapted to future technological developments as will be apparent to one of ordinary skill in the art. The present should be understood to include such additional embodiments.

This section describes, first, preferred classes of ambulatory MPM signals input to this invention and illustrative systems for their capture, described next are preferred processing methods, beginning with a preferred integration of individual methods and followed by the individual methods and examples.

5.1 Preferred Signals

Preferred embodiments of the present invention monitor a subject moment-by-moment cardiac and pulmonary functioning, activity level, and associated or other physiological systems or processes. Particular embodiments may monitor fewer physiological systems, while other embodiments may monitor additional physiological systems depending on the availability of ambulatory, non-invasive sensors.

Respiratory sensors gather signals sensitive to respiratory rate and/or tidal volume. Such sensors may directly measure air flows or volumes at the mouth and nose using one of the many known technologies for such measurements. Preferably, the respiratory sensors are less intrusive. A preferred class of such sensors, relying on the known two-compartment model of breathing, measure indicia of thorax and abdominal sizes, such as volumes, cross sectional areas, circumferences, diameters, and the like, and obtain an overall tidal volume signal from combinations of these two size signals. These sizes can be measuring by sensors based on one of the many known technologies for such measurements, such plethysmography and especially inductive plethysmography ("IP"). Illustrative IP respiratory sensors are subsequently described.

Cardiac sensors gather signals sensitive to the electrical and/or mechanical functioning of the heart. Electrical functioning can be routinely recorded by one, two, or more electrocardiographic (ECG) leads conductively affixed to the subject. Mechanical functioning is extracted from non-invasively gathered signals sensitive to moment-by-moment volumes of one or more of the cardiac chambers ("cardiac pulsation" signals). A preferred class of such sensors measures chest pulsations arising chiefly from functioning of the left ventricle. Such chest pulsations are known to clinicians and are usually maximum in the mid-thorax at the level of the xiphoid process, and can accordingly be measured by sensors sensitive to indicia of mid-thorax size, such as volume, a cross sectional area, circumference, diameter, and the like. However, most chest wall motion is produced by respiration, and cardiac-derived pulsations represent no more that 1-5% of total signal amplitude. Illustrative cardiac sensors based on IP technology are subsequently described.

Activity level signals can be processed for the physiological content. In this invention, they also advantageously provide a reference for artifacts in signals from other sensors generated by subject motion. Subject accelerations are often reflected in non-invasive sensor signals, especially in signals from sensors sensitive to indicia of subject sizes such as thorax or abdominal sizes. Accordingly, moment-by-moment activity levels signals preferably gathered by one or more accelerometers sensitive to total subject acceleration provide a usefully accurate reference for such motion artifacts. Alternatively, individual sensors can include individual accelerometers sensitive to accelerations local to the sensor, and the reference signal generated will more accurately remove motion artifacts present in the individual sensor signals. Additional sources of artifacts may be present in some environments, and if sensors sensitive to these additional artifact sources are available, their output can provide a reference for such additional artifact signals. For example, electromagnetic interference can generate artifacts, and may possibly be monitored by signals gathered by conducting or magnetic "antenna" arrangements.

Many associated or other physiological systems or processes may be useful in particular embodiments, and their sensors can be useful in MPM monitoring. For example, temperatures measured by thermistors or similar devices and/or blood oxygen saturation (or blood saturation activity) measured by pulse oximeters can often usefully associated with parameters of cardio-respiratory functioning. Additionally, electroencephalogram ("EEG") signals (or cerebral electrical activity) are often useful, and can be measured by one, two, or more leads conductively affixed to the patient's head. EEG signals can be used to monitor general subject alertness, to monitor sleep stages during sleep studies, and for other purposes. Electro-oculogram ("EOG") signals or electro-myogram ("EMG") signals can be usefully gathered along with EEG signals.

Additional input signals can be selected from the variety of known preferably non-invasive physiological sensors, and include, without limitation, skin conductance signals, and electrical and./or magnetic impedance signals sensitive to the functioning of internal systems such as respiratory or cardiac systems, sound and ultrasound signals, and the like.

5.2 Exemplary Systems

Exemplary systems can be conceptually divided for descriptive purposes into monitoring subsystems, which include the sensors that gather signals for processing, and processing subsystems, which provide platforms for executing this invention's processing methods.

Turning first to exemplary monitoring subsystems, and in particular to their included sensors, one of ordinary skill will appreciate that these sensors can be constructed according to the many known technologies useful for non-invasive physiological sensing. It is routine that selected sensors should have sufficient accuracy and precision, both in amplitude and response time (bandwidth), so that signals gathered actually reflect the physiological systems and processes of interest in an embodiment. Preferably, the sensors have clinically confirmed accuracies and precisions.

Specifically, several signals gathered in preferred embodiments of this invention arise from sensors measuring indicia of subject sizes, such as cross sectional areas, circumferences, diameters, or geometrically similar indicia, of selected portions of the subject's torso, neck, extremities, or other body part. Such sensors are simply referred to herein as "cross sectional size sensors" or as "size sensors". Size sensors are known that are based on diverse technologies, including magnetometers; strain gauges using magnetic, mechanical or optical means; optical techniques including interferometry; electrical impedance; surface electrical or magnetic activity; plethysmography, inductive plethysmography, ultrasonic and doppler measurements of body wall motions or body diameters; and so forth. Such sensors are useful for the present invention. Exemplary size sensors based on inductive plethysmographic (IP) technology are summarized subsequently.

This invention is directed to monitoring subsystems configured so that a subject is not constrained and can perform their normal daily waking and sleeping activities (referred to herein as "ambulatory monitoring subsystems"). Preferably, the monitoring subsystems are also configured for subject use without assistance by medical or other trained personnel. An exemplary monitoring subsystem configuration is as a wearable item, for example, a garments, a bands, a patch, and the like, into which sensors are incorporated.

Figure 1B:
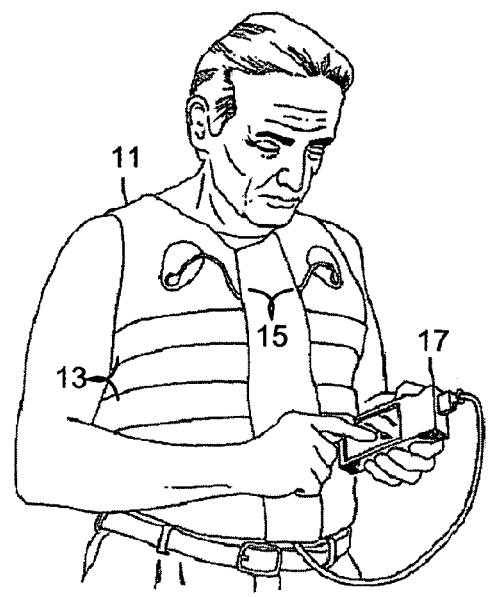
Figure 1C:
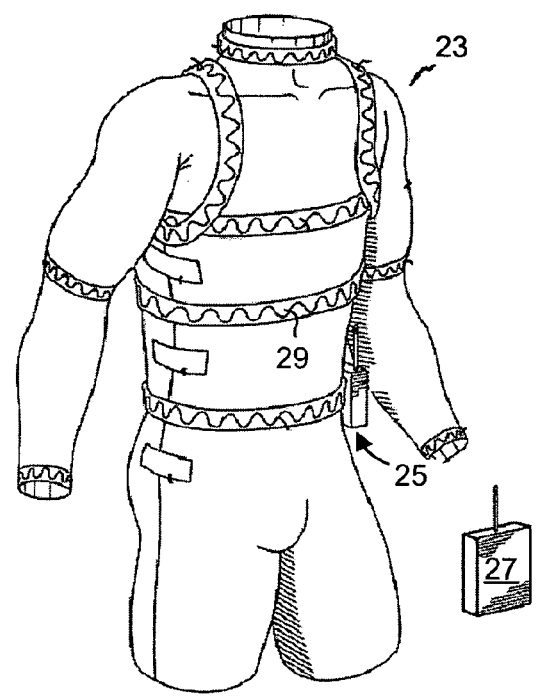
Figure 1D:
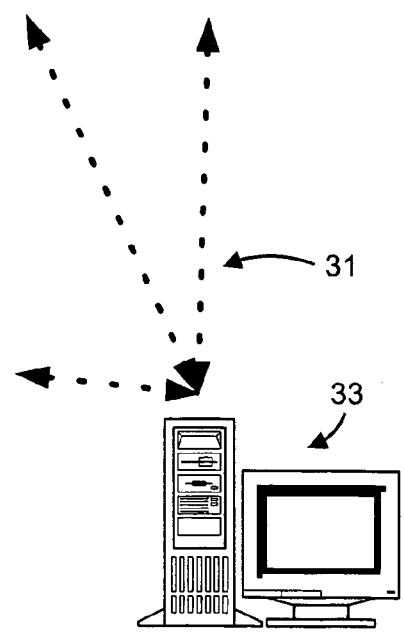

Exemplary wearable monitoring subsystems are illustrated in FIGS. 1A-C. FIG. 1A illustrates band 19 that can be worn about a subject's torso permitting vigorous, unconstrained activity, and that can incorporate size sensors sensitive to respiratory and/or cardiac pulsation activity, accelerometers, ECG sensors, temperature sensors, and so forth. Signals gathered by band 19 are locally transmitted to and buffered in wrist-mounted local unit 21. From unit 21 they are transmitted for analysis. Local unit 21 may also perform methods of this invention.

FIG. 1B illustrates shirt 11 that incorporates two or more size sensors 13 two lead ECG 15, and optionally additional sensors, such as accelerometers, pulse oximeters, $CO_2$ sensors, EEG (and EOG and EMG) sensors, temperature sensors, and the like. The size sensors are preferably sensitive at least to rib cage (RC) and abdomen (AB) sizes so that tidal volume may be determined according to a two-component lung model. Local unit 17 is a handheld computer for buffering signals, re-transmitting signals, performing certain methods, allowing user feedback and interaction, and the like.

Finally, FIG. 1C illustrates garment 23 equipped with a more extensive array of size capable of measuring venous and arterial pulsations, individual lung function, and the like, as well as other sensors. In particular, size sensor 29 at the mid-thorax level of the xiphoid process returns signals with cardiac pulsation components. This embodiment is provided with two buffering and/or processing units, local unit 25 and nearby unit 27.

Signals gathered by monitoring systems for use by this invention are processed according to the method's of this invention on the processing subsystem, which can include one or more analysis computers providing processing capability that may be variously located or distributed. In one embodiment, basic signal processing, e.g., filtering and digitization, is performed on units local to the monitoring subsystem, such as local units 17, 21, and 25. Complete processing by this invention's methods generally requires processing capabilities similar to those of a modern desktop PC with, for example, a 2 Ghz or more processor, 256 Mb or more of main memory, 10 Gb or more of peripheral storage, standard interface units, and the like. In one embodiment, nearby unit 27 provides this capability in the vicinity of the monitored subject, while in another embodiment illustrated in FIG. 1D this capability is provided by remotely located system 33. Signal data gathered is transferred system 31 (and to unit 27) by routine means, for example, wirelessly using private wireless networks or the public cellular phone system; by means of a memory device such as a micro hard disk or a flash memory card, and the like.

This invention's methods are routinely coded in standard computer languages, such as C++, or in known higher level languages, such as Matlab and Matlab toolboxes (Math Works, Natick, Mass.), and then translated or compiled into executable computer instructions. These instructions are typically loaded into the processing subsystems from computer readable media (such as CD ROMS, flash cards, etc.), across network connections, and the like.

Summary of Inductive Plethysmography

An exemplary (non-limiting) technology for implementing size sensors is inductive plethysmography (IP), and the following summarize IP technology. IP sensors determine indicia of size by measuring the self-inductance of a conductive loop configured about the subject in a plane of interest. The conductive loop is wearably configured, such as by incorporation in elastic band, to closely follow size changes of the enclosed body part by corresponding changes in the loop's self-inductance, which is then measured by incorporating the loop in a resonant circuit and measuring changes in resonant frequency, for example, by counting oscillating current pulses in known periods of time.

Respiration data is preferably gathered by two IP size sensors about the ribcage ("RC") and abdomen ("AB"). This data can be combined to yield a lung volume and/or tidal volume signal. Clinical studies comparing IP determined tidal volumes with pneumo-tachographic airflow measurements have reported correlation accuracies of r=0.96 and greater. Cardiac pulsation data may be gathered by an IP sensor about the mid-thorax that returns signals, although dominated by respiratory components does include extractable cardiac components, from which indicia of moment-by-moment cardiac volumes, cardiac output, and ventricular wall motion, and the like can be extracted. IP sensors about extremities or neck return signals reflecting arterial and venous pulses.

Details of IP technologies may be found in numerous issued US patents and pending US patent applications, all of which are incorporated herein by reference in their entireties for all purposes. See, for example, U.S. Pat. No. 6,783,498 issued Aug. 31, 2004 for determining ventricular volumes; U.S. Pat. No. 6,551,252 issued Apr. 22, 2003 for an ambulatory IP system; U.S. Pat. No. 6,413,225 issued Jul. 2, 2002 for calibrating tidal volumes; U.S. Pat. No. 6,341,504 issued Jan. 29, 2002 for stretchable conductive fabric; U.S. Pat. No. 6,047,203 issued Apr. 4, 2000 for an ambulatory IP system. Also see, for example, U.S. Pat. No. 5,331,968 issued Jul. 26, 1994 for IP sensors and circuitry; U.S. Pat. No. 5,301,678 issued Apr. 12, 1994 for IP transducer; U.S. Pat. No. 5,178,151 issued Jan. 12, 1993 for IP measurement of cardiac output; U.S. Pat. No. 5,159,935 issued Nov. 3, 1992 for IP measurement of measuring individual lung function; U.S. Pat. No. 5,040,540 issued Aug. 20, 1991 for IP measurement of central venous pressure.

Additional less current information may be found in U.S. Pat. No. 4,986,277 issued Jan. 22, 1991 for IP measurement of central venous pressure; U.S. Pat. No. 4,834,109 issued May 30, 1989 for calibrating tidal volumes; U.S. Pat. No. 4,815,473 issued Mar. 28, 1989 for monitoring respiration; U.S. Pat. No. 4,807,640 issued Feb. 28, 1989 for IP transducer; U.S. Pat. No. 4,456,015 issued Jun. 26, 1984 for IP measurement of neck volume; U.S. Pat. No. 4,452,252 issued Jun. 5, 1984 for IP measurement of cardiac parameters from neck volumes); U.S. Pat. No. 4,373,534 issued Feb. 15, 1983 for calibrating tidal volumes; U.S. Pat. No. 4,308,872 issued Jan. 5, 1982 for monitoring respiration.

Monitoring subsystems based on IP sensor technology useful in the present invention are available from VivoMetrics, Inc., Ventura, Calif.

5.3 Preferred Processing Methods

In preferred embodiments, several of this invention's individual processing methods are linked into an integrated system that processes MPM signal from a monitoring subsystem primarily directed to cardio-respiratory monitoring. The integrated arrangement is described first, and is followed by detailed descriptions of its component steps.

In particular embodiment gathering fewer signals, portions of the integrated system are not needed and may be dispensed with. In other particular embodiments, additional classes of physiological signals may be gathered, and the integrated system may be expanded to process the additional classes in a manner analogous to the cardio-respiratory classes. Further, one of skill in the art will appreciate that the detailed interconnections to be described may be altered while still achieving the intent of this invention.

5.3.2 Integration of Processing Steps

FIG. 2 illustrates a preferred processing arrangement useful for cardio-respiratory, ambulatory, MPM monitoring. In this figure, processing steps are indicated by boxes; data flow is indicated by lines; and steps that may be eliminated or bypassed are indicated in dashed outline. Ambulatory monitoring subsystem 43 gathers a basic (and exemplary) set of cardio-respiratory monitoring signals (MPM) from monitored subject 41. Respiratory signals gathered include two size sensor signals preferably from the subject's RC and AB (labeled "respiration" in FIG. 2); cardiac signals gathered include size sensor signal from the mid-thorax having a cardiac component (labeled "thorax"); activity level signals include a one to three axis accelerometer signal used in part as a reference for motion artifacts (labeled "motion"); and an EEG signal from a single EEG sensitive lead (labeled "EEG").

Filtering and preprocessing 45 generally represents the preliminary processing of raw sensor signals, such as analog filtering, sampling and re-sampling, digital filtering, and the like. This pre-processing is configured as known in the arts in order to output digital signals free of aliasing and with a bandwidth and quantization sufficient to represent intended physiological systems and/or processes. Some substantive processing may also be performed at this stage, for example, the two-component respiratory signals can be combined to yield a third respiratory signals sensitive to tidal volume (Vt). Alternatively, all substantive processing may be delayed until after motion artifact removal. IP-derived signal preprocessing is described in detail in the previously referenced patents relating to IP technology.

Experience with ambulatory MPM has taught that sufficiently vigorous subject activity usually generates significant motion artifact in many of all sensor signals, especially in size respiratory and cardiac size sensor signals. Motion artifact may also be occasionally present even in EEG signals. Because the motion artifact component may almost completely swamp physiological components, it is preferably removed prior to any further processing by, e.g., step 53 for respiratory signals, by step 55 for thorax (cardiac) signals, and by optional step 57 for EEG signals.

Motion artifacts are removed from an individual signal by jointly processing the individual signal along a motion artifact reference signal that represents the causative subject motions. In a preferred embodiment, the motion artifact reference signal is derived from one or more accelerometers worn by the subject. This signal can optionally be high and low pass filtered to separate out motion signals from posture signals, respectively (described in detail in several of the IP patent previously included). The filtered motion signals are used as the motion artifact reference, while the posture signals can be separately useful physiological data. Alternately, separate accelerometers may be mounted with sensors and their signals used to remove motion artifacts only from the associated sensors.

In certain embodiments, sensor signals may contain additional artifacts, and if a representative "artifact" signal, e.g., signal 47, is available, it can be combined 49 with the motion artifact signal so that these additional artifacts may also be removed. Alternately separate processing steps may be dedicated to removing additional artifacts using their reference signals. Electromagnetic interference is a frequent source of such an additional artifacts.

Experience with ambulatory MPM has also taught that the non-invasive sensors used often return signals having contributions from two or more physiological systems or processes. It is usually physiological useful to separate these signals into data primarily reflective of the functioning of individual physiological systems or processes. But separation by inspection or even by conventional filtering of single signals fails is often not possible because the individual contributions combined in the sensor signals have widely differing amplitudes and/or overlapping spectrums. However, it has been discovered that separation of such signals is usefully possible by joint processing of two or more such signals, each signal having different relative contributions of each of the two or more physiological systems or processes using adaptive processing techniques. Accordingly, such signal separation steps are additionally included following artifact removal.

In particular, respiration often produces large amplitude movements, and sensors often return signals including undesired respiration components along with components of interest. Signals are often mixed with signals from other physiological systems. Accordingly, processing step 61 jointly processes respiration and thorax signals to separate signals primarily reflective of actual cardiac pulsation activity. Respiration components can also be present in EEG signals and can optionally be removed by processing step 59. Further, signals from other sensors (not illustrated) may be similarly processed if undesired respiration components are present. In other embodiments, sensor signals may include combinations of other physiological processes and/or systems, and if so, their joint processing is advantageous to produce more useful physiological data. Methods used are similar to those to be subsequently described for removing respiratory components.

Furthermore, joint processing of two or more such signals, each signal having different relative contributions of each of two or more physiological systems or processes using adaptive processing techniques is useful in cases where two or more physiological systems or processes interact with each other in physiologically significant manners (instead of simply leading to sensor signals with undesired components). Joint processing in such cases can produce data in which such interactions are more clearly apparent. In particular, heart rate variability ("HRV") and/or respiratory sinus arrhythmia ("RSA") is an example such an interaction arising in cardiorespiratory monitoring, and its identification 63 is subsequently described in detail. These interactions can be clearly identified in the spectra output from this step. Joint processing of other physiological interactions often must be specially designed in view of the particular interaction to be identified, but such design is routine in view of principles to be described in connection with HRV and RSA.

5.3.3 Individual Processing Steps

Individual processing steps 53, 55, 57, 59, 61, and 63 (FIG. 2), and examples of their functioning, are now described in detail.

Removal of Motion Artifacts from Respiratory Signals

FIGS. 3A-B illustrate separating respiratory signals from motion artifacts by adaptive processing of the respiratory signals along with a reference signal sensitive to subject motion. These figures illustrate RC signal processing; processing of other respiratory signals, e.g., AB or Vt signals, is closely similar.

For improved separation, it has been discovered advantageous that all signals being jointly processed in a single filtering step be sampled at the same sampling rate and/or at coincident sampling times. Since input (preprocessed) sensor signals are often sampled at rates specific to the different sensor types, re-sampling steps are advantageously precede filtering. Preferably, this re-sampling is to the lowest sampling rate among the input signals as long as any down-sampling of any input signal does not result in loss of relevant information. In the illustrated embodiment, "RC in" (rib cage size signals) signals are sampled at 50 Hz, while "ACC in" (accelerometer motion reference signals) are sampled at 10 Hz. Thus, step 71 down-samples "RC in" by a factor of 5 to 10 Hz to the sampling rate of "ACC in".

Further, removal of signal mean values from certain signals has also been discovered to improve separation. For respiratory processing, removal of the mean from the RC and the ACC signals is advantageous, and steps 73 and 79 are interposed to remove these means. In this case, signal means have been found to only slowly vary when the subject maintains a single posture, and can removed by simply subtracting a running average for a time typical of a single posture, e.g., 30 sec.

Steps 77 and 83 actually separate motion artifacts present in "RC in". Adaptive filtering is used in many individual methods of this invention, and is now generally described in detail. Specific implementations of adaptive filtering for the separate methods are described in connection with the methods themselves.

Adaptive filtering process a primary signal having desired components mixed with undesired components in order to enhance the desired components at the expense of the undesired components. Preferably, an output signal from an adaptive filter is dominated by the desired components. Importantly, the filter does not need to be adjusted in advance to the expected characteristics of the desired and undesired components, but instead "learns" these characteristics from the input signals. The reference signal specifically "teaches" characteristics of the undesired components, and therefore preferably (strongly) correlates with these component in the primary signal.

Specifically, the input reference signal is linearly filtered so that it is similar to the undesired components in the primary signal, and then combined with (subtracted from) the primary signal to yield an error signal. The adaptive filer adjusts the linear filter coefficients (weights), preferably sample-by-sample, to minimize the error signal. Since the minimized error signal is the primary signal from which the filtered reference signal has been removed, it contains the desired signal components with enhanced amplitude. Conversely, the filtered reference signal, as stated, closely resembles the undesired components present in the input primary signal. Either the filtered reference signal or the error signal (that is the corrected primary signal) can be further processed. See, e.g., Widrow et al., 1985, *Adaptive Signal Processing*, Pearson Education Inc. (included herein by reference in its entirety for all purposes).

The linear filter may be finite impulse response (FIR) type or infinite impulse response type (IIR); in this invention FIR filters are preferred because, compared to IIR filters, FIR filters are phase linear and allow weight adjustment that are more stable with less computational requirements. However, IIR filters may be used in other embodiments where the computational resources are adequate. Although IIR filters are not usually phase linear, they can provide sharper filtering with fewer coefficients than FIR filters.

Many methods are known for adjusting FIR filter coefficients (weights). See, e.g., Widrow et al., chaps. 6 and 8. A preferred but non-limiting method is known as the least mean square (LMS) method, which is a practical approach to adjusting filter coefficient in real-time without computationally-intensive matrix inversions (and without requiring any prior statistical knowledge of the signals). Specifically, the LMS method computes filter coefficients that minimize the mean squared error (MSE) of the error signal by a steepest decent method where all filter weights are updated time-sample-by-time-sample. At each iteration, the LMS method reduces the MSE. The LMS method determines coefficients that both converge from an initial estimate and also adjust to time variations in primary and reference signal characteristics.

In detail, the LMS method proceeds as follows. At each time sample, k, k>0, the filtered reference signal, $y_k$, is determined as usual for a FIR filter:

$$y_k = \sum_{i=0}^{N-1} w(k)_i r_{k-i} \qquad (1)$$

Here, the input reference signal at time k−i<k is $r_{k-i}$, $w(k)_i$ are the coefficients, i=1 ... N, at time k, and N is the filter length. The filtered reference signal is then subtracted from the primary signal, $p_k$, to yield the error signal, $z_k$.

$$z_k = p_k - y_k \qquad (2)$$

Either of both of $p_k$ and $z_k$ is then further processed. The set of N filter coefficients is usually initialized to zero at the first time sample: „ where N is the length of FIR filter, are initialized usually to zero:

$$w(0)_i = 0 \qquad (3)$$

At subsequent time samples, all filter coefficients are then updated according to:

$$w(k+1)_i = w(k)_i + 2\mu z_k p_{k-i} \qquad (4)$$

where μ is a convergence parameter that controls the rate of convergence and stability of the LMS method.

Generally, filter length, N, is chosen in dependence on the amount of memory available for the filter, the desired convergence rate, the desired filter characteristics (sharpness, etc.), signal bandwidths, and the like. Longer filters take longer to converge and can excessively smooth the desired signal component, whilst shorter filters may not properly filter a reference signal to remove a sufficient amount of the undesired signal component. In this invention, filter length are generally from approximately 15 to 140 depending on the signals being jointly processed. A typical filter length for respiratory signals is approximately 20, which can be adjusted but was found to me more than adequate. The convergence parameter, μ, can be manually chosen based on observing adaptive filter performance or can be chosen automatically by methods known in the art. It has been found that once the convergence parameter is properly chosen, the adaptive filter is stable and converges in a number of sampling times approximately 1.3 times the length of the FIR filter. The parameter μ can be as small as approximately $10^{-9}$ when processing signal that have not been normalized to comparable ranges. When the input and reference signals are normalized by dividing the signal by its maximum sample for that time segment, convergence factors of μ=0.01 to 0.001 provided good convergence rates.

Continuing now with the details of motion artifact removal from respiratory signals, respiratory signal 75 including motion artifact resulting from the subject's motion is the primary input signal, and accelerometer 81 signal (motion signal) is the reference signal. The reference signal is filtered by adaptive filter 83, and then filtered reference signal 85 is combined 77 with primary signal 75 resulting in error signal 87. The filter weights are adapted so that the error signal is minimized, in other words, so that as much as possible of the motion artifact is subtracted from the primary signal. The error signal with enhanced respiratory components is as "RC out".

FIG. 3B illustrates motion artifact removal from respiratory signals monitored from a strenuously sprinting subject. Here, the subject is sprinting at approximately 3 steps per second and taking approximately 3 steps per breath (approximately 1 breath per second). The first signal band in FIG. 3B illustrates a portion of the "RC in" signal 75 in which motion artifact virtually completely swamps the respiration signal. Clearly, manually separating the respiratory component from the motion artifact is difficult if not impossible. The second signal band illustrates a corresponding portion of input accelerometer signal 81 reflecting subject motion. Each positive spike in this signal identifies each step of the subject as the subject's foot leaves the ground and causes a sudden upward acceleration.

The third signal band illustrates adaptively filtered acceleration signal 85. Close examination show that the adaptive filter has caused a varying phase lag from of the filtered reference signal from the input reference signal, but has left signal spectrum largely unchanged. The fourth signal band illustrates signal 87 the "RC out" signal, which is the input primary signal with the filtered reference signal subtracted. It can be appreciated that most of the undesired motion artifact has been eliminated leaving a resulting signal with the subject's respiratory rib cage motions considerably enhanced and clearly apparent. The fifth signal band, with "RC in" and "RC out" superimposed, illustrates how the respiratory component is almost completely swamped by motion artifact component.

This example illustrates the effectiveness of this motion artifact removal method.

Removal of Motion Artifacts from Other Signals

Motion artifacts are removed from other signals, in particular the thorax signal in step 55 and the EEG signal in step 57, with techniques substantially similar to those described above for motion artifact removal from respiratory signals.

In situations of less strenuous subject motion, motion artifacts may have such a reduced amplitude in EEG signal that their removal in step 57 may be bypassed. Bypassing motion artifact removal can be automatically controlled. For example, if a running average of power in the motion reference signal falls below a predetermined threshold value, artifact removal can be bypassed. If the power is above the threshold, artifact removal is performed. The threshold can be pre-determined differently for different monitoring signal inputs.

Cardiac Signal Extraction

Thorax signals, "THORAX in" preferably from a mid-thorax size sensor, often have desired cardiac pulsation components with amplitudes no more 1% to 5% of the amplitudes of the undesired respiratory components. It has been discovered that reliable extraction of this relatively small cardiac component requires consideration of two reference signals: a respiratory reference signal and an ECG reference signal. The respiratory reference signal is "RC in", because signals from a rib cage size sensor have been to correlate most closely with the undesired respiratory component in "THORAX in". The ECG signal is processed to extract an R wave signal.

The rightmost portion of FIG. 4 illustrates ECG signal processing. First, R waves are identified 113 using software or hardware means known in the art, for example, the Pan and Tomkins QRS detection algorithm. Prior to R wave identification 113, the "ECG in" signal, which can arise from one or more ECG leads, is interpolated and up-sampled to 1 kHz from its input sampling rate, which is often 200 Hz.

Next, it is preferred but optional to discard R waves 115 that can be identified as ectopic or artifact. An R wave is identified as ectopic if it occurs in an unexpected temporal relation with respect to the adjacent R waves by being, e.g., more than a threshold time interval before or after the expected time of R wave occurrence determined from a recent mean heart rate. Mean heart rate can be determined from a running average of R-R interval lengths, e.g., from an average of the prior 10 sec of R-R intervals lengths. A preferred threshold time interval threshold is approximately 100 msec. If motion artifact is not removed from "ECG in" signals, an R wave is also identified as ectopic if it occurs during sufficiently intense subject motion, e.g., when an accelerometer motion sensor signal exceeds a threshold value, preferably 0.5-1.5 g. Alternatively, motion artifact may be removed from the ECG as described above (either at all times, or only when the acceleration exceeds the above threshold). Identified ectopic R wave are discarded from the R wave signal. Optionally a synthetic R wave is interpolated into the R wave signal at the expected R wave occurrence time.

Lastly, an output R wave signal is constructed. For cardiac filter extraction, the output R wave signal preferably identifies the times of R wave occurrences. For HRV analysis, the output R wave signal preferably identifies time intervals between sequential R waves. Both output signal are advantageously sampled at 50 Hz.

The leftmost portion of FIG. 4 illustrates cardiac signal extraction. Pre-processing 45 of the thorax signal preferably includes band pass filtering with a lower corner frequency of approximately 0.4 Hz (range 0.2-0.5 Hz) and an upper corner frequency of approximately 10-15 Hz (range 10-30 Hz). This filtering rejects low and high frequency non-cardiac components. Next, motion artifact is removed (55 in FIG. 2) from the thorax signal (and from the respiratory signal) generating "THORAX in".

Since it again has been found that filtering is improved if all signals are sampled at the same rate and/or coincidently, re-sampling step 101 performs any necessary re-sampling. In the illustrated embodiment, "THORAX in" is down-sampled to 50 Hz from an original 200 Hz sampling rate in order to match "RC in" and the processed R wave signal which are both sampled at 50 Hz. Optionally, the extracted cardiac signal can be re-sampled 107, e.g., back to 200 Hz, prior to output. Other common re-sampling frequencies, e.g., 100 Hz instead of 50 Hz, may be also be used.

After any necessary re-sampling, adaptive filter 103 processes the "THORAX in" primary signal using "RC in" as a reference signal. The adaptive filter is preferably a FIR filter with length approximately 120 (range 60-140) and weights adjusted according to the LMS method as previously described in detail. Different embodiment employ alternative adaptive filters (IIR filters, lattice filters, and the like) and different weight adaptation methods. Filter output is the error signal in which differences between the primary thoracic size sensor signal and the filtered motion reference signal are minimized so that desired cardiac components are enhanced while undesired respiratory components are decreased. In many situations, the cardiac components in the error signal have been sufficiently enhanced so that the error signal is useful without additional processing. In these situations, further processing 105 may be bypassed, and the error signal itself may be up-sampled, output, and/or input to cardiac feature extraction 111.

In many other situations, the error signal must be further processed because it still contains significant artifact. Because this remaining artifact often does not strongly correlate, or correlate at all, with available reference signals, e.g., motion signals, other artifact signals, respiratory signals, other sensor signals, and so forth, further adaptive processing as described is not advantageous. However, although the remaining undesired artifact components also do not correlate with the R-wave occurrence signal output by ECG processing, the desired cardiac components naturally do strongly correlated with these R wave occurrence times. Thus, the R-wave signal may be used to identify and select the cardiac components from the artifact components (instead of, as in the adaptive processing above, using a reference signal to identify and select the undesired artifact components). A preferred identification and selection method is ensemble averaging, which has been found to usually largely eliminate all remaining artifact.

In detail, ensemble averaging 105 uses the R-wave occurrence signal output by ECG processing as a reference "clock" according to which physiologically corresponding times in previous cardiac cycles can be identified and the signals at these corresponding times selected and averaged. Since the undesired artifact at these times are not correlated while the desired cardiac signal is strongly correlated at these times, ensemble averaging will further enhance the desired cardiac components while minimizing remain artifact components. Relatively simple ensemble averaging over 5-50 prior cardiac cycles with constant weights is preferred when its performance is adequate. The following equation describes the preferred ensemble averaging:

$$\hat{f}(n, t) = 1/M \sum_{i=0}^{M-1} f(t - R_{M-1-i}) \qquad (5)$$

where $R_0$ is the R-wave occurrence nearest to sample time t, and $R_{M-1-i}$ are the M−1 previous R-waves in reverse temporal order.

Lastly, the processed signal may be re-sampled 107 to the desired output sampling frequency. Since the extracted cardiac signal usually closely corresponds to the actual cardiac volume, parameters of cardiac functioning can be determined 111. For example, the amplitude of the extracted cardiac signal is an indicia of stroke volume; the amplitude times heart rate provides an indicia of cardiac output. The time from an R-wave peak to the subsequent amplitude maximum of the extracted cardiac signal provides an indicia pre-ejection period. The minimum of the derivative of the extracted cardiac signal (remembering that as heart contracts, its volume decreases) provides an indicia of the peak ejection rate. Other cardiac parameters known in the art may similarly be determined. Further, the extracted cardiac signal can be used to detect and track ventricular motion abnormalities, and changes in detected ventricular motion over time can provide much of the same clinical information now detectable only with imaging techniques such as ultrasound.

Figure 5A:
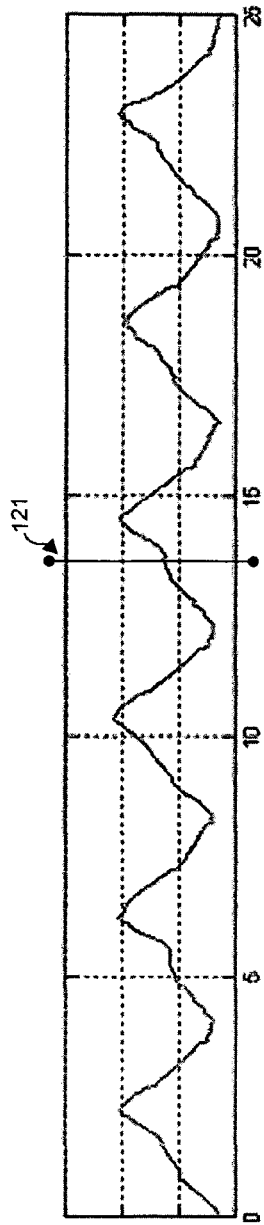
Figure 5B:
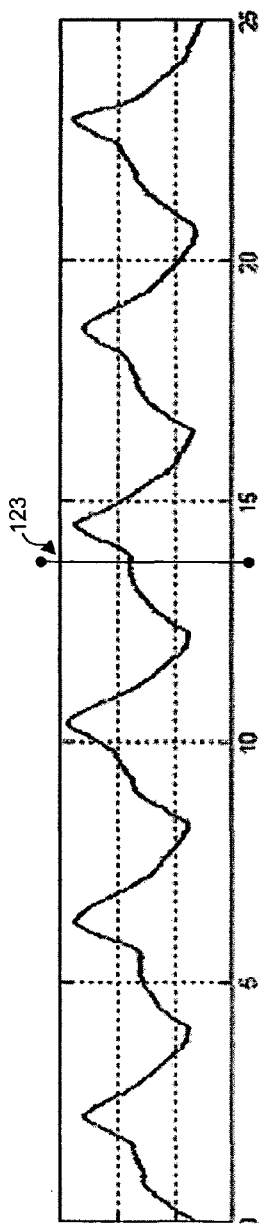
Figure 5C:
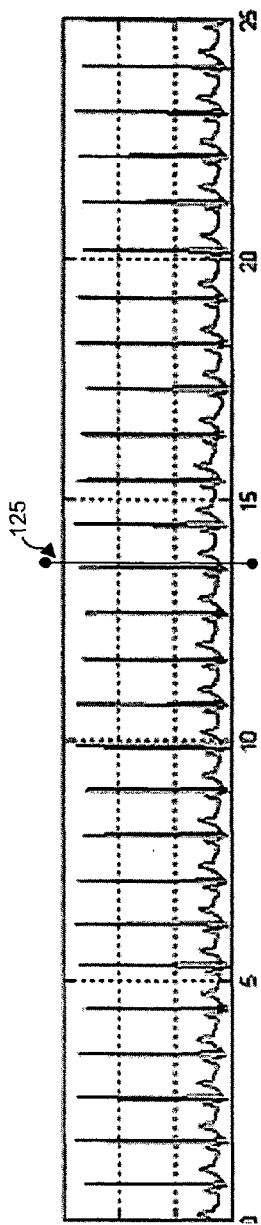
Figure 5F:
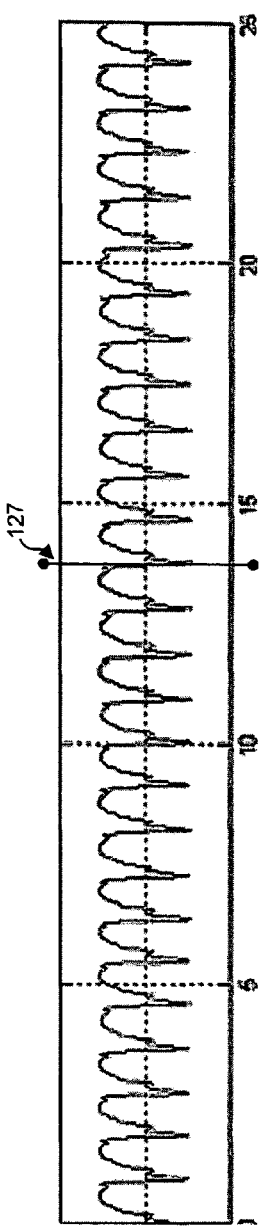
Figure 5D:
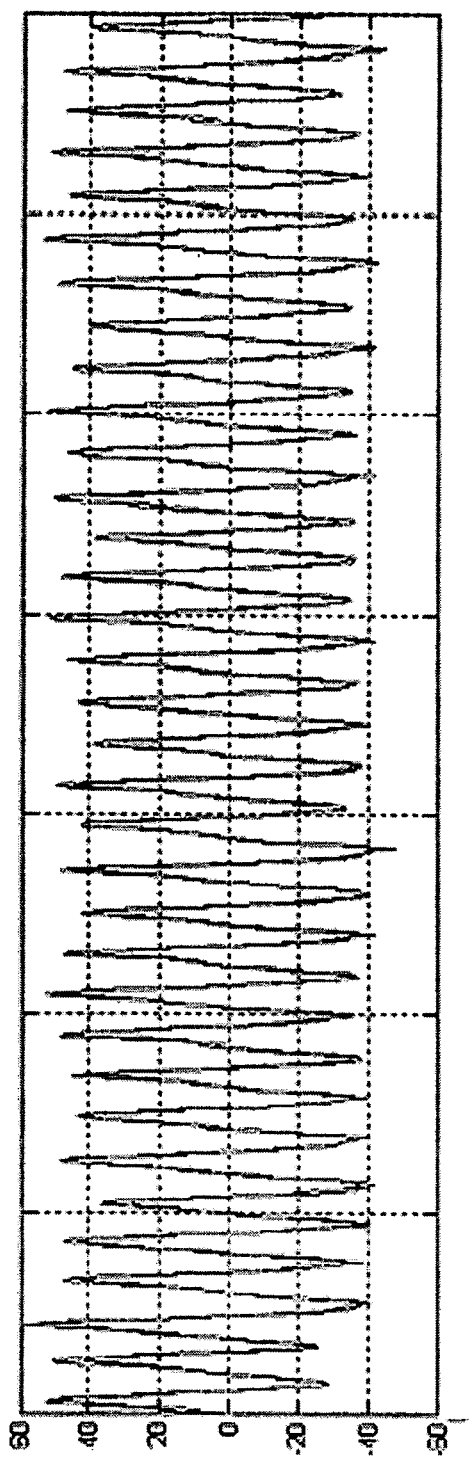
Figure 5E:
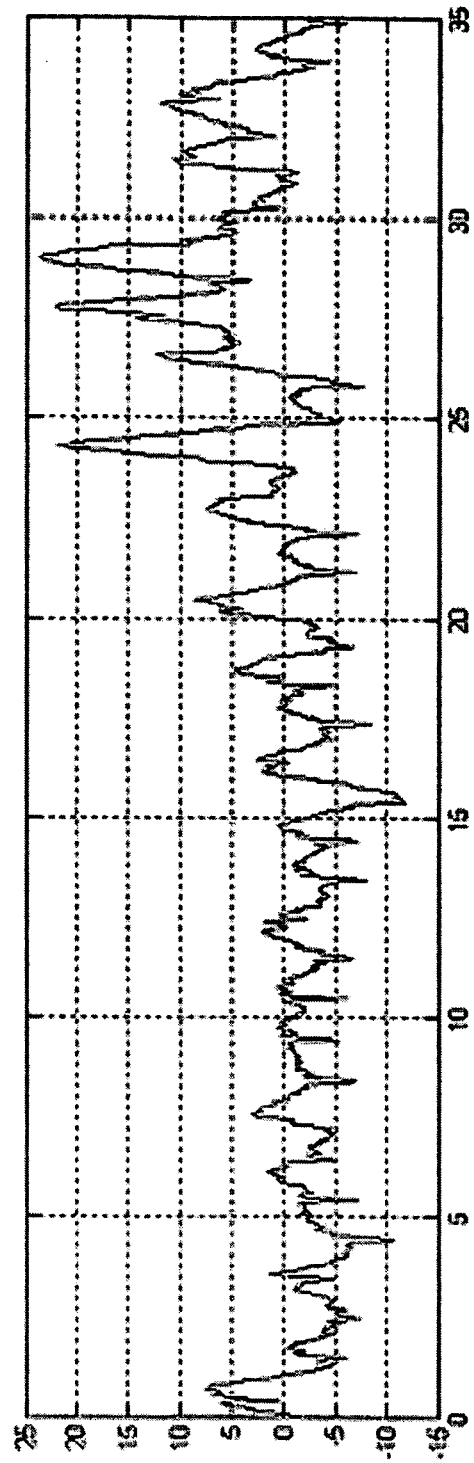

FIGS. 5A-F illustrate an actual example cardiac signal extraction. FIGS. 5A-C and F are 25 sec concurrent samples of the "THORAX in" signal (prior to adaptive filtering), the "RC in" signal, the "ECG in" signal, and the "CARDIAC out" signal (subsequent to ensemble averaging), respectively. FIG. 5D is a 150 sec. trace of respiratory signal after filtering by the adaptive FIR filter; and FIG. 5E is a 35 sec. trace of the output of adaptive filter 103 (prior to ensemble averaging) output. In this example, the TCG signal was down-sampled to 50 Hz prior to adaptive filtering; the adaptive FIR filter had 120 stages; the convergence factor was $\mu \approx 2 \times 10^{-8}$; and the filter coefficients converged from zero initial values in about 150 time cycles, or 3 sec at 50 Hz.

First, comparing the "THORAX in" signal of FIG. 5A with the "RESP. (RC) in" signal of FIG. 5B it is apparent that: the cardiac motion component appears at most as small irregularities in the "THORAX in" signal superimposed on the considerably larger respiratory motion component and roughly coincident with the R-waves in the ECG signal; and the respiratory motion components of the "THORAX in" and "RC in" signals are similar. Comparing the unfiltered "RC in" signal of FIG. 5B with the FIR filtered "RC in" signal of FIG. 5D, it is apparent that the adaptive FIR filter makes the "RC in" more similar to "THORAX in" signal's respiratory component.

Next, comparing the adaptive-filter output of FIG. 5E with the input "THORAX in" signal of FIG. 5A, it is apparent that: the adaptive filter has removed nearly all of the undesired respiratory component, leaving artifact, noise, and residual respiratory component; and cardiac motion (particularly systolic contractions) is more readily apparent. Comparing the adaptive-filter output of FIG. 5E with the ensemble average output of FIG. 5F, it is apparent that the ensemble average has eliminated nearly all of the remaining undesired components. The cardiac component can be seen to generally comprise periodic beats with slower diastolic inflow followed by rapid systolic outflow. Even finer details of the cardiac motion component are also apparent.

For ease of further comparison, temporally coincident gridlines have been placed in FIGS. 5A-C and F at approximately 14 secs. In the "THORAX in" signal of FIG. 5A at 121, a very small, but perceptible, irregularity due to the cardiac motion component in superimposed on the respiratory motion component. However, close examination of the "RC in" signal of FIG. 5B at 123 reveals that no cardiac motion component is apparent. The extracted cardiac motion signal of FIG. 5F illustrates peak of systolic ejection at coincident time 127, while the ECG of FIG. 5C at 125 shows that an R wave, representing ventricular depolarization, slightly precedes mechanical ejection at coincident time 508, measuring the delay between the R wave and mechanical systole known in the art.

EEG Signal Extraction

Studying subject sleep is one application of ambulatory multiple parameter physiological monitoring systems. Although a sleeping subject is not "ambulatory" in the sense of actively walking, etc., monitoring during unconstrained, normal sleep can provide a more realistic record of sleep activities. Thus, ambulatory MPM system are of use even in sleep monitoring.

Sleep monitoring (also other monitoring tasks) is benefited by data from which a subject's mental state can be classified as either awake, or drowsy, or sleep, and sleep can be classified as either stage I or II or III sleep or REM sleep. Since mental state monitoring is routinely performed be examining electroencephalogram (EEG) records (and optionally electro-oculogram (EOG) electro-myogram (EMG) records), processing EEG signals from ambulatory MPM systems is described. Processing of EOG and EMG signal is similar to EEG signal processing.

Such processing is preferably configured in view of the following EEG signal characteristics. EEG signals frequently contain undesired artifact at least because the recorded electrical activity has small amplitudes, often no more than 10's of micro-volts, more readily contaminated with undesired components such as noise and influences from other physiological systems. In particular, EEG signals often contain respiratory components of amplitudes similar to or greater than the EEG signal amplitudes. On the other hand, EEG signals processing should be substantially amplitude and phase linear over the range of physiologically significant frequencies from less than 4 Hz to greater than 30 Hz (referred to in order of increasing frequency as delta, theta, alpha, and beta waves). Additionally, mainly during sleep, EEG signals may include brief higher frequency bursts (spindles, K complexes, and the like) that should be linearly processed.

FIG. 6A illustrates one preferred method for separating undesired respiratory components from desired EEG components in signals recorded from one or more EEG leads. To preserve frequencies, amplitudes, and phases, "EEG in" signal 161 passes directly without processing to output stage 157 where "EEG out" signal 159 is constructed by subtracting estimated respiratory components 153. Adaptive FIR filter 151 determines the estimated respiratory components by filtering respiratory reference signal 149, and the adaptive filter weights are adjusted to minimize an error signal 155 determined as the difference between EEG primary signal 143 and filtered reference signal 153. When error signal 155 is minimized, the filtered respiratory reference signal represents the respiratory components as closely as possible. In summary, the respiratory components, represented by the adaptively filtered respiratory reference signal, are used to construct the adaptive filter error signal from a filtered EEG primary signal and also to construct "EEG out" from an unfiltered EEG reference signal. The error signal, representing the respiratory components in the filtered EEG reference signal, is not output. Adaptive processing is preferred to fixed bandwidth filters because the frequency spectrum of the undesired respiratory component can overlap the lower end of the EEG signal frequency spectrum.

The primary are reference signal are processed before use by adaptive filter 151. The respiratory reference signal preferably arises from a rib cage size sensor, as the RC signal best correlates with the undesired respiratory components in the EEG signal. In the illustrated embodiment, the "RC in" is sampled at 50 Hz and the "EEG in" signal is sampled at 128 Hz. To have adaptive filter inputs coincidently sampled as is preferred, the "RC in" is up-sampled 147 to 128 Hz; down-sampling "EEG in" is undesirable since significant high frequency information can be lost. The up-sampled respiratory reference signal 149 is then input to the adaptive filter.

It has been found that filter performance is improved by low-pass filtering 141 the primary EEG signal to block higher frequency EEG components while passing all components in the frequency range of the respiratory reference signal. Accordingly, the "EEG in" is first passed through low pass filter 141 that allows most of the respiratory signal to pass while blocking much of the EEG signal. Filter 141 preferably has an upper corner frequency at approximately 1.4 Hz (range 1-2 Hz). Such low pass filtering of the primary signal is believed to improve filter performance because, first, it increases the power of the undesired respiratory component in the primary input signal, and second, such increased power permits the adaptive filter to more accurately minimize the error signal because the relative decrease of the error signal is greater FIG. 6B is an example of removing respiratory components from an EEG signal. The first signal band in FIG. 6B is "EEG in" signal 161, which is seen to contain lower-amplitude, higher-frequency components superimposed on larger-amplitude, lower-frequency components. The second signal band is RC reference signal 149, which is seen to reflect largely steady breathing at about 15 breaths per minute. The third signal band is the adaptively filtered RC reference signal 153 which predicts the actual respiratory component in "EEG in". The fifth signal band superimposes the "EEG in" signal with predicted respiratory component 153. It can now be appreciated that much of the larger-amplitude, lower-frequency components in "EEG in" are of respiratory origin, while all the lower-amplitude, higher-frequency components are of EEG origin. The fourth band is "EEG out" signal 159 which include the higher-frequency EEG components without detectable respiratory components.

Analysis of HRV and RSA

Heart rate variability (HRV) refers to alterations in heart rate often measured from variations of RR intervals. HRV has many physiological uses, and is further useful in assessing cardiovascular disease. Generally, heart rate is influenced by the autonomic nervous system (ANS), in particular by the fluctuating balance between the sympathetic and parasympathetic (vagal) branches of the ANS. Chemoreceptor processes, thermoregulation, and the rennin-angiotensin system are believed to cause very low frequency HRV, below approximately 0.04 Hz. A low frequency (LF) component between 0.04 Hz and 0.15 Hz is believed to reflect the balance of sympathetic and parasympathetic branches of the ANS. Finally, direct vagal (parasympathetic) modulation of the sino-atrial node causes high-frequency band (HF) HRV between approximately 0.15 to approximately 0.4 Hz or higher. Vagal activity is usually strongly influenced by respiration, and the resulting HF modulation found predominantly at respiratory frequencies is known as respiratory sinus arrhythmia (RSA).

Heretofore, HRV and RSA amplitude have determined by time domain, phase domain, and frequency domain approaches. In time-domain approaches, maximum and minimum values of R-R time intervals are measured within the bounds of each breath. In phase domain approaches, RSA is determined by analyzing heart rate dynamics with respect to respiratory phase. Finally, HRV is often spectrally analyzed by Fourier transforming appropriately windowed time R-R interval time series (windows reduce spectral leakage and filter random noise). None of these approaches is entirely satisfactory, often because absence of respiratory reference signals makes difficult determining the origin of measured HRV components.

FIG. 6A illustrates improved HRV and RSA analysis methods and systems of this invention which adaptively filter and R-R interval primary signal using a respiratory reference signal. The primary signal is "RR in" 173, an R-R interval signal derived, e.g., by processing an ECG signal by methods described with respect to FIG. 4. An RR interval signal is piecewise constant, each constant piece representing the length immediately previous R-R interval. In the illustrated embodiment, "RR in" is sampled at 50 Hz and down-sampled (decimated) 175 by a factor of 10 to 5 Hz. Since HRV frequencies of interest are generally less than 0.5 Hz of less, a 5 Hz sampling rate provides an adequate signal representation. It has been found that the adaptive filter convergence is improved if its baseline (zero frequency component) is at zero. Accordingly, the baseline may be removed 177 (also referred to as "de-trending") after down-sampling and prior to the adaptive filter by subtracting the mean of a preferably 5 minute signal segment using a best straight line fit. However, for particular uses, it may be advantageous to retain the average RR interval value (zero frequency component). In these cases, de-trending 177 is bypassed.

The preferred secondary reference signal is the tidal volume, Vt, which has been found to correlate most closely with respiratory modulation of heart rate. This signal can be derived, as explained in one or more of the above referenced US patent relating to IP technology, from a combination of signals of rib cage and abdomen size sensor signals, and in the embodiment is sampled at 50 Hz. Adaptively filtered signals are preferably sampled coincidently on at the same frequency, and Vt in is accordingly down-sampled (decimated) 185 to 5 Hz to match the RR sampling frequency. Prior to down-sampling extraneous signal components are removed by low pass filter 171, which has preferred upper corner frequency of approximately 1.4 Hz (range 1-2 Hz). As above, this processing does not lose physiological information as frequencies of interest in HRV analysis are generally less than 0.5 Hz of less.

Next, signals 179 and 187 are adaptively filtered 189 and 181, preferably with a FIR type filter employing LMS method for weight adjustment. Error signal 191 results from subtracting the adaptively filtered Vt signal from the RR signal. An adaptive filter length of approximately 20 has been found adequate for the illustrated HRV analysis. Varying filter length from 20 did not significantly improve HRV analysis. The filter convergence parameter, $\mu$, was advantageously in the range of approximately $2.5 \times 10^{-9}$ to approximately $2 \times 10^{-8}$, the low values resulting from use non-normalized input signals. As input signal characteristics change, filters parameters can be adjusted either manually or automatically (here and in the previously described LMS adaptive-filtering examples) with programmable features common in most signal processing software packages.

As explained, the highest frequency (HF) components in the HRV spectra are usually due to respiratory modulation (RSA), the other components are usually of lower frequencies LF) and are due to other influences. Since adaptively filtered Vt signal 193 is as close as possible to the respiratory components in the RR signal, this signal primarily contains the HF HRV components, that is the RSA components. Conversely minimized error signal 191, having had the HF components subtracted 181, primarily contains the LF HRV components believed to be due to other than respiratory influences.

In embodiments where an RR interval signal retaining the LF components of variability including the zero frequency component, the average RR interval, preliminary de-trending 177 is bypassed, and signal 191 is output. Then de-trending is performed 177" just prior to spectral analysis. In other embodiments, de-trending 177 is performed since is often results in more rapid filter convergence, while de-trending 177" is bypassed. In all cases, RR signal de-trending is preferably prior to spectral analysis (and may be entirely bypassed if spectral analysis is omitted).

Spectral analysis of the LF signal 195 and the HF signal 197 may be performed by many of the spectral analysis techniques known in the art. A preferred techniques is Welch's averaged, modified periodogram method, which analyzes a signal section-by-section with adjacent sections overlapping by 50% overlap. Prior to Fourier transforming, each section is windowed, preferably with a Hamming window although other known window functions may be used, e.g., Blackman-Harris, or Nutal, or the like. Rectangular windows are not preferred as they normally introduce spectral leakage. The combined results of the LF and HF spectra, signals 199 and 201, respectively, jointly represent the full spectrum of HRV, and the HF spectra alone represents RSA. Optionally, the power in the LF and HF frequency bands may be calculated across the ranges 0.04-0.15 and 0.14-0.4 Hz, respectively.

FIGS. 8A-10B illustrate three examples of the above described HRV analysis. Each example has an analysis of separate 6-7 min segments of data extracted from a continuous 16 hour ambulatory MPM record obtained with LifeShirt™ (VivoMetrics, Inc., Ventura, Calif.). For 8 hours of the 16 hour period, the subject was awake, ambulatory, and performing normal daily tasks. For the remaining 8 hours, the subject was sleeping without any constraint on motions during sleep. A tidal volume signal, Vt, was obtained from monitored RC and AB signals and an RR signal was derived as described above.

FIGS. 8A-B, FIGS. 9A-B, and 10A-B all illustrate similar signals. In FIGS. 8A, 9A, and 10A, the first two signal bands are input Vt signal 183 and input RR signal 173 sampled at 50 Hz (and, for the Vt signal, low pass filtered), respectively, while the second two signal bands are these signals downsampled to 5 Hz, that is signals 187 and 179 (and, for the RR signal, linearly de-trended), respectively. The fifth signal band is adaptively filtered Vt signal, which is the component of the RR signal predicted to correlate with breathing, that is the RSA component. The sixth signal band is RR signal 191 with the HF component subtracted but retaining the LF HRV components. In FIGS. 8B, 9B, and 10B, the top two spectra are of RR signal 179 and Vt signal 187, while the bottom two spectra are of HF (RSA) component 201 and of LF component 199.

It can be appreciated by examining the illustrated spectra that HRV differs in each of the three examples; in particular, the relative amount of RSA compared to LF variability can vary considerably. Further, it is readily apparent that in all examples RSA has been cleanly separated from the LF HRV due to other causes. In fact, except for perhaps a few percent of spectral leakage, the RSA and LF variability have been completely separated. Additionally, little or no smoothing has occurred; the spectral details of the separated signals preserve well the details of the spectra of the original RR signal.

QT Interval Correction

Turing to FIG. 11, which is a schematic of an ECG cardiac cycle, the QT interval in the ECG is the time interval (usually specified in milliseconds) between a Q wave (the first component of the QRS complex) and the immediately following T wave. Electro-physiologically, the QRS complex represent systolic depolarization of the ventricles; the T wave represents ventricular re-polarization; and the QT interval is the represents an approximate plateau period of ventricular depolarization. This interval is of considerable importance: its prolongation is associated with increased risk for malignant ventricular arrhythmia and sudden cardiac death in post myocardial infarction patients; and new drug evaluations must now include assessment of a drug's effects on the QT length.

Determining the QT interval is complicated by its strong dependence upon the length of the preceding cardiac cycle (e.g., the preceding RR interval). A useful determination of the QT interval should correct for this RR interval effects and many techniques for making this correction and determining a corrected QT interval, QTc, have been described in the art. One common technique is due to Bazett and is simply expressed by the following equation:

$$QT_c = \frac{QT}{\sqrt{RR}}, \tag{6}$$

where: QTc is the QT interval corrected for heart rate; QT is the measured interval between the Q wave and the following T wave; and RR is the measured RR interval (specified in seconds). See, e.g., Bazett, 1920, An analysis of time-relations of electrocardiogram. Heart 7:353-370. Another common technique for QT interval correction uses a linear regression model expressed by the following equation:

$$QT_{LC} = Qt + 0.154(1 - RR), \tag{7}$$

where: $QT_{LC}$ is the linearly corrected QT interval, and RR is the measured RR interval. See, e.g., Sagie et al., 1992, An improved method for adjusting the QT interval for heart rate (the Framingham Heart Study). *Am J Cardiol;* 70:797-801. Limitations of these techniques include over-correction of the QT interval at high heart rates, or lack or verification in ambulatory conditions or limited predictive power (the linear regression model accounting for only approximately 46%, r=0.68, of QT interval variance).

This invention provides improved systems and method for QT correction that utilize the results of the previously described HRV and RSA analysis. Although direct parasympathetic (vagal) modulation of the QT interval is believed to be relatively unimportant, indirect effects due to the variations in heart rate (HRV) because of parasympathetic input to the sino-atrial node are significant, often to the extent of obscuring the baseline QT interval and its changes. As described, a major component of HRV is due to respiratory influences (RSA), and this invention's methods and systems clearly separate HRV into RSA and non-respiratory LF components.

In a first improved correction method, the QT interval is corrected according to the known corrections techniques but previous RR interval measures are replaced by RR interval signal 203 (FIG. 7) with LF HRV but excluding HF RSA variability. Thereby, QTc reflects LF HRV with obscuring effects from RSA eliminated. For example, the previously mentioned QTc correction techniques become:

$$QT_c = \frac{QT}{\sqrt{RR_{203}}} \quad (8)$$

and $$QT_{LC} = Qt + 0.154(1 - RR_{203}) \quad (9)$$

where $RR_{203}$ refers to signal 203 in FIG. 7.

In another improved correction method, the QT can be corrected by performing on a QT interval signal the same processing as illustrated in FIG. 7 for the RR interval signal. A QT interval signal may be derived from an ECG signal in the same manner as the RR signal is derived. The LF QT variability spectra represents slower variations in the QT interval not related to respiratory influences on heart rate. The HF QT variability spectra represents the indirect respiratory influences on the QT interval. Also, use of respiratory variables in addition to RSA will allow for a more informed and accurate estimation of the QTc correction.

Use of either of these improved QT correction techniques permits a more accurate QTc estimate, and accordingly a more accurate estimate of other influences, e.g., an administered drug, on the QT interval.

The invention described and claimed herein is not to be limited in scope by the preferred embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

A number of references are cited herein, the entire disclosures of which are incorporated herein, in their entirety, by reference for all purposes. Further, none of these references, regardless of how characterized above, is admitted as prior to the invention of the subject matter claimed herein.

What is claimed is:

1. A method for processing primary sensor signals monitored from a subject and arising from a plurality of sensors sensitive to a plurality of physiological systems or processes of the monitored subject, said method comprising:
   adaptively enhancing desired physiological components relative to undesired artifact components in one or more of said primary sensor signals monitored from said subject during periods comprising unconstrained activity using an analysis computer to yield one or more adaptively enhanced sensor signals;
   adaptively enhancing components sensitive to desired physiological systems or processes relative to components sensitive to other undesired physiological systems or processes in at least one of said one or more of adaptively enhanced sensor signals using said analysis computer; and
   processing said primary sensor signals jointly with one or more reference sensor signals, wherein said primary sensor signals and said one or more reference sensor signals are sampled at the same sampling rate.

2. A method for processing primary sensor signals monitored from a subject and arising from a plurality of sensors sensitive to a plurality of physiological systems or processes of the monitored subject, said method comprising:
   adaptively enhancing desired physiological components relative to undesired artifact components in one or more of said primary sensor signals monitored from said subject during periods comprising unconstrained activity using an analysis computer to yield one or more adaptively enhanced sensor signals;
   adaptively enhancing components sensitive to desired physiological systems or processes relative to components sensitive to other undesired physiological systems or processes in at least one of said one or more adaptively enhanced sensor signals using said analysis computer; and
   processing said primary sensor signals jointly with one or more reference sensor signals, wherein said primary sensor signals and said one or more reference sensor signals are sampled at the same sampling rate,
   wherein said one or more of said reference sensor signals comprise signals sensitive to subject motion activity.

3. A method for processing primary sensor signals monitored from a subject and arising from a plurality of sensors sensitive to a plurality of physiological systems or processes of the monitored subject, said method comprising:
   adaptively enhancing desired physiological components relative to undesired artifact components in one or more of said primary sensor signals monitored from said subject during periods comprising unconstrained activity using an analysis computer to yield one or more adaptively enhanced sensor signals;
   adaptively enhancing components sensitive to desired physiological systems or processes relative to components sensitive to other undesired physiological systems or processes in at least one of said one or more adaptively enhanced sensor signals using said analysis computer; and
   processing said primary sensor signals jointly with one or more reference sensor signals, wherein said primary sensor signals and said one or more reference sensor signals are sampled at the same sampling rate,
   wherein said one or more reference sensor signals are sensitive to said undesired physiological systems or processes.

4. A method for processing primary sensor signals monitored from a subject and arising from a plurality of sensors sensitive to a plurality of physiological systems or processes of the monitored subject, said method comprising:
   adaptively enhancing desired physiological components relative to undesired artifact components in one or more of said primary sensor signals monitored from said subject during periods comprising unconstrained activity using an analysis computer to yield one or more adaptively enhanced sensor signals;
   adaptively enhancing components sensitive to desired physiological systems or processes relative to components sensitive to other undesired physiological systems or processes in at least one of said one or more adaptively enhanced sensor signals using said analysis computer; and
   processing said primary sensor signals jointly with one or more reference sensor signals, wherein said primary sensor signals and said one or more reference sensor signals are sampled at the same sampling rate,
   wherein said one or more reference sensor signals comprise components correlating with said undesired components in said primary sensor signals.

5. A method for processing primary sensor signals monitored from a subject and arising from a plurality of sensors sensitive to a plurality of physiological systems or processes of the monitored subject, said method comprising:
   adaptively enhancing desired physiological components relative to undesired artifact components in one or more of said primary sensor signals monitored from said subject during periods comprising unconstrained activity using an analysis computer to yield one or more adaptively enhanced sensor signals;

adaptively enhancing components sensitive to desired physiological systems or processes relative to components sensitive to other undesired physiological systems or processes in at least one of said one or more adaptively enhanced sensor signals using said analysis computer; and processing said primary sensor signals jointly with one or more reference sensor signals, wherein said primary sensor signals and said one or more processed reference sensor signals are sampled at a sampling rate, wherein said primary sensor signals and said one or more processed reference sensor signals are sampled at the same sampling rate; and re-sampling one or more primary sensor signals at a sampling rate, wherein the one or more primary sensor signals are sampled at the same sampling rate.

6. A method for processing primary sensor signals monitored from a subject and arising from a plurality of sensors sensitive to a plurality of physiological systems or processes of the monitored subject, said method comprising:

adaptively enhancing desired physiological components relative to undesired artifact components in one or more of said primary sensor signals monitored from said subject during periods comprising unconstrained activity using an analysis computer to yield one or more adaptively enhanced sensor signals;

adaptively enhancing components sensitive to desired physiological systems or processes relative to components sensitive to other undesired physiological systems or processes in at least one of said one or more adaptively enhanced sensor signals using said analysis computer; and processing said primary sensor signals jointly with one or more reference sensor signals, wherein said primary sensor signals and said one or more reference sensor signals are sampled at the same sampling rate; and reducing an error signal, said error signal being a difference between said processed primary sensor signals and said processed reference sensor signals.

7. A method for processing primary sensor signals monitored from a subject and arising from a plurality of sensors sensitive to a plurality of physiological systems or processes of the monitored subject, said method comprising:

adaptively enhancing desired physiological components relative to undesired artifact components in one or more of said primary sensor signals monitored from said subject during periods comprising unconstrained activity using an analysis computer to yield one or more adaptively enhanced sensor signals;

adaptively enhancing components sensitive to desired physiological systems or processes relative to components sensitive to other undesired physiological systems or processes in at least one of said one or more adaptively enhanced sensor signals using said analysis computer; and processing said primary sensor signals jointly with one or more reference sensor signals, wherein said primary sensor signals and said one or more reference sensor signals are sampled at the same sampling rate, wherein said adaptively enhancing desired physiological components comprises joint processing with at least one of said one or more reference signals, wherein said at least one reference signal is sensitive to subject motion activity.

8. A method for processing primary sensor signals monitored from a subject and arising from a plurality of sensors sensitive to a plurality of physiological systems or processes of the monitored subject, said method comprising:

adaptively enhancing desired physiological components relative to undesired artifact components in one or more of said primary sensor signals monitored from said subject during periods comprising unconstrained activity using an analysis computer to yield one or more adaptively enhanced sensor signals;

adaptively enhancing components sensitive to desired physiological systems or processes relative to components sensitive to other undesired physiological systems or processes in at least one of said one or more adaptively enhanced sensor signals using said analysis computer; and processing said primary sensor signals jointly with one or more reference sensor signals, wherein said primary sensor signals and said one or more reference sensor signals are sampled at the same sampling rate, wherein said step of adaptively enhancing components sensitive to said desired physiological systems or processes comprises joint processing with a reference signal sensitive to said undesired other physiological systems or processes.

9. A method for processing primary sensor signals monitored from a subject and arising from a plurality of sensors sensitive to a plurality of physiological systems or processes of the monitored subject, said method comprising:

adaptively enhancing desired physiological components relative to undesired artifact components in one or more of said primary sensor signals monitored from said subject during periods comprising unconstrained activity using an analysis computer to yield one or more adaptively enhanced sensor signals;

adaptively enhancing components sensitive to desired physiological systems or processes relative to components sensitive to other undesired physiological systems or processes in at least one of said one or more adaptively enhanced sensor signals using said analysis computer; and processing said primary sensor signals jointly with one or more reference sensor signals, wherein said primary sensor signals and said one or more reference sensor signals are sampled at the same sampling rate, wherein said primary sensor signals comprise electrocardiograph (ECG) signals and said one or more reference signals comprise respiratory signals, wherein said adaptively enhancing enhances respiratory components in a heart rate (HR) signal derived from said ECG signals, said enhanced signal comprising a high frequency heart rate variability (HF HRV) signal; and generating a low frequency heart rate variability (LF HRV) signal comprising components in said HR signal other than said enhanced respiratory components.

10. A method for processing primary sensor signals monitored from a subject and arising from a plurality of sensors sensitive to a plurality of physiological systems or processes of the monitored subject, said method comprising:

adaptively enhancing desired physiological components relative to undesired artifact components in one or more of said primary sensor signals monitored from said subject during periods comprising unconstrained activity using an analysis computer to yield one or more adaptively enhanced sensor signals;

adaptively enhancing components sensitive to desired physiological systems or processes relative to components sensitive to other undesired physiological systems or processes in at least one of said one or more adaptively enhanced sensor signals using said analysis computer; and processing said primary sensor signals jointly with one or more reference sensor signals, wherein said primary sensor signals and said one or more reference sensor signals are sampled at the same sampling rate, wherein said primary sensor signals comprise electrocardiograph (ECG) signals and said one or more reference signals comprise respiratory signals, wherein said step of adaptively enhancing enhances respiratory components in a heart rate (HR) signal derived from said ECG signals, said enhanced signal comprising a high frequency heart rate variability (HF HRV) signal;

generating a low frequency heart rate variability (LF HRV) signal comprising components in said HR signal other than said enhanced respiratory components; and estimating one or more corrected QT intervals dependent on QT intervals measured in said ECG signals and on said LF HRV signal.

* * * * *